United States Patent
Xi et al.

(10) Patent No.: US 11,179,376 B2
(45) Date of Patent: Nov. 23, 2021

(54) SALTS OF PYRAZOLO[1,5-A]PYRIDINE DERIVATIVE AND USE THEREOF

(71) Applicants: SUNSHINE LAKE PHARMA CO., LTD., Guangdong (CN); CALITOR SCIENCES, LLC., Newbury Park, CA (US)

(72) Inventors: Ning Xi, Newbury Park, CA (US); Mingming Sun, Guangdong (CN)

(73) Assignee: SUNSHINE LAKE PHARMA CO., LTD., Dongguan (CN)

( * ) Notice: Subject to any disclaimer, the term of this patent is extended or adjusted under 35 U.S.C. 154(b) by 0 days.

(21) Appl. No.: 16/221,449

(22) Filed: Dec. 15, 2018

(65) Prior Publication Data
US 2020/0222376 A1    Jul. 16, 2020

Related U.S. Application Data

(60) Provisional application No. 62/608,330, filed on Dec. 20, 2017.

(51) Int. Cl.
*C07D 471/04* (2006.01)
*A61K 31/444* (2006.01)
*A61K 45/06* (2006.01)

(52) U.S. Cl.
CPC ............ *A61K 31/444* (2013.01); *A61K 45/06* (2013.01); *C07D 471/04* (2013.01)

(58) Field of Classification Search
CPC ..... A61K 31/444; A61K 45/06; C07D 471/04
USPC .......................................................... 514/303
See application file for complete search history.

(56) References Cited

U.S. PATENT DOCUMENTS 9,573,953 B2 *    2/2017    Xi ........................ A61K 31/519

FOREIGN PATENT DOCUMENTS

WO    WO-2014130375 A1 *    8/2014    .............. A61P 43/00

* cited by examiner

*Primary Examiner* — Rita J Desai
(74) *Attorney, Agent, or Firm* — Oliff PLC

(57) ABSTRACT

The present invention provides salts of pyrazolo[1,5-α] pyridine derivative and use thereof. The invention also relates to a pharmaceutically acceptable composition comprising such salts and a method of using the salts and the pharmaceutically acceptable composition to prevent or treat a proliferative disorder or pulmonary fibrosis in a patient.

8 Claims, 11 Drawing Sheets

SALTS OF PYRAZOLO[1,5-A]PYRIDINE DERIVATIVE AND USE THEREOF

CROSS-REFERENCE TO RELATED APPLICATIONS

This application claims the benefits of U.S. Provisional Application No. 62/608,330 filed on Dec. 20, 2017, which is hereby incorporated by reference in their entirety.

FIELD OF THE INVENTION

The invention relates to salts of pyrazolo[1,5-α]pyridine derivatives and use thereof, specifically relates to salt of N-(5-(3-cyanopyrazolo[1,5-α]pyridin-5-yl)-2-methoxypyridin-3-yl)-2,4-difluorobenzenesulfonamide (compound of formula (I)) and use thereof, further relates to composition containing said salts above. The salts or the composition can be used to inhibit/modulate protein kinases, further prevent, manage or treat proliferative disorders or pulmonary fibrosis in a patient.

BACKGROUND OF THE INVENTION

The phosphoinositide 3-kinases (PI3 kinases or PI3Ks), a family of lipid kinases, have been found to play key regulatory roles in many cellular processes including cell survival, proliferation and differentiation. The PI3K enzymes consist of three classes with variable primary structure, function and substrate specificity. Class I PI3Ks consist of heterodimers of regulatory and catalytic subunits, and are subdivided into 1A and 1B based on their mode of activation. Class 1A PI3Ks are activated by various cell surface tyrosine kinases, and consist of the catalytic p110 and regulatory p85 subunits. The three known isoforms of Class 1A p110 are p110α, p110β, and p110δ, which all contain an amino terminal regulatory interacting region (which interfaces with p85), a Ras binding domain, and a carboxy terminal catalytic domain. Class 1B PI3Ks consist of the catalytic (p110γ) and regulatory (p101) subunits and are activated by G-protein coupled receptors. ("Small-molecule inhibitors of the PI3K signaling network" *Future Med. Chem.*, 2011, 3, 5, 549-565).

As major effectors downstream of receptor tyrosine kinases (RTKs) and G protein-coupled receptors (GPCRs), PI3Ks transduce signals from various growth factors and cytokines into intracellular massages by generating phospholipids, which activate the serine-threonine protein kinase AKT (also known as protein kinase B (PKB)) and other downstream effector pathways. The tumor suppressor or PTEN (phosphatase and tensin homologue) is the most important negative regulator of the PI3K signaling pathway. ("Status of PI3K/Akt/mTOR Pathway Inhibitors in Lymphoma." *Clin Lymphoma, Myeloma Leuk,* 2014, 14 (5), 335-342.)

The signaling network defined by phosphoinositide 3-kinases (PI3Ks), AKT and mammalian target of rapamycin (mTOR) controls most hallmarks of cancer, including cell cycle, survival, metabolism, motility and genomic instability. The pathway also contributes to cancer promoting aspects of the tumor environment, such as angiogenesis and inflammatory cell recruitment. The lipid second messenger produced by PI3K enzymes, phosphatidylinositol-3,4,5-trisphosphate (PtdIns(3,4,5)P3; also known as PIP3), is constitutively elevated in most cancer cells and recruits cytoplasmic proteins to membrane-localized 'onco' signalosomes.

Cancer genetic studies suggest that the PI3K pathway is the most frequently altered pathway in human tumors: the PIK3CA gene (encoding the PI3K catalytic isoform p110α) is the second most frequently mutated oncogene, and PTEN (encoding phosphatase and tensin homolog, the major PtdIns(3,4,5)P3 phosphatase) is among the most frequently mutated tumor suppressor genes. In accord, a recent genomic study of head and neck cancer found the PI3K pathway to be the most frequently mutated. Indeed, even in cancer cells expressing normal PI3K and PTEN genes, other lesions are present that activate the PI3K signaling network (that is, activated tyrosine kinases, RAS and AKT, etc.). As a net result of these anomalies, the PI3K pathway is activated, mutated or amplified in many malignancies, including in ovarian cancer (Campbell et al., *Cancer Res.,* 2004, 64, 7678-7681; Levine et al., *Clin. Cancer Res.,* 2005, 11, 2875-2878; Wang et al., *Hum. Mutat.,* 2005, 25, 322; Lee et al., *Gynecol. Oncol.,* 2005, 97, 26-34), cervical cancer, breast cancer (Bachman et al., *Cancer Biol., Ther.,* 2004, 3, 772-775; Levine et al., supra; Li et al., *Breast Cancer Res. Treat.,* 2006, 96, 91-95; Saal et al., *Cancer Res.,* 2005, 65, 2554-2559; Samuels and Velculescu, *Cell Cycle,* 2004, 3, 1221-1224), colorectal cancer (Samuels et al., *Science,* 2004, 304, 554; Velho et al., *Eur. J. Cancer,* 2005, 41, 1649-1654), endometrial cancer (Oda et al., *Cancer Res.,* 2005, 65, 10669-10673), gastric carcinomas (Byun et al., *M. J. Cancer;* 2003, 104, 318-327; Li et al., supra; Velho et al., supra; Lee et al., *Oncogene,* 2005, 24, 1477-1480), hepatocellular carcinoma (Lee et al., id), small and non-small cell lung cancer (Tang et al., *Lung Cancer* 2006, 11, 181-191; Massion et al., *Am. J. Respir Crit. Care Med.,* 2004, 170, 1088-1094), thyroid carcinoma (Wu et al., *J. Clin. Endocrinol. Metab.,* 2005, 90, 4688-4693), acute myelogenous leukemia (AML) (Sujobert et al., *Blood,* 1997, 106, 1063-1066), chronic myelogenous leukemia (CML) (Hickey et al., *J. Biol. Chem.,* 2006, 281, 2441-2450), glioblastomas (Hartmann et al., *Acta Neuropathol (Berl),* 2005, 109, 639-642; Samuels et al., supra), Hodgkin and non-Hodgkin lymphomas ("PI3K and cancer: lessons, challenges and opportunities", *Nature Reviews Drug Discovery,* 2014, 13, 140).

The PI3K pathway is hyperactivated in most cancers, yet the capacity of PI3K inhibitors to induce tumor cell death is limited. The efficacy of PI3K inhibition can also derive from interference with the cancer cells' ability to respond to stromal signals, as illustrated by the approved PI3Kδ inhibitor idelalisib in B-cell malignancies. Inhibition of the leukocyte-enriched PI3Kδ or PI3Kγ may unleash antitumor T-cell responses by inhibiting regulatory T cells and immune-suppressive myeloid cells. Moreover, tumor angiogenesis may be targeted by PI3K inhibitors to enhance cancer therapy. ("Targeting PI3K in Cancer: Impact on Tumor Cells, Their Protective Stroma, Angiogenesis, and Immunotherapy", *Cancer Discov.,* 2016, 6 (10), 1090-1105.)

mTOR is a highly conserved serine-threonine kinase with lipid kinase activity and participates as an effector in the PI3K/AKT pathway. mTOR exists in two distinct complexes, mTORC1 and mTORC2, and plays an important role in cell proliferation by monitoring nutrient availability and cellular energy levels. The downstream targets of mTORC1 are ribosomal protein S6 kinase 1 and eukaryotic translation initiation factor 4E-binding protein 1, both of which are crucial to the regulation of protein synthesis. ("Present and future of PI3K pathway inhibition in cancer: perspectives and limitations", *Current Med. Chem.,* 2011, 18, 2647-2685).

Knowledge about consequences of dysregulated mTOR signaling for tumorigenesis comes mostly from studies of pharmacologically disruption of mTOR by repamycin and its analogues such as temsirolimus (CCI-779) and everolimus (RAD001). Rapamycin was found to inhibit mTOR and thereby induce G1 arrest and apoptosis. The mechanism of rapamycin growth inhibition was found to be related to formation of complexes of rapamycin with FK-binding protein 12 (FKBP-12). These complexes then bound with high affinity to mTOR, preventing activation and resulting in inhibition of protein translation and cell growth. Cellular effects of mTOR inhibition are even more pronounced in cells that have concomitant inactivation of PTEN. Antitumor activity of rapamycin was subsequently identified, and a number of rapamycin analogues such as temsirolimus and everolimus have been approved by the US Food and Drug Administration for the treatment certain types of cancer.

Fibrosis is the formation of excess fibrous connective tissue in an organ or tissue in a reparative or reactive process. Examples of fibrosis include, but are not limited to pulmonary fibrosis, liver fibrosis, dermal fibrosis, and renal fibrosis. Pulmonary fibrosis, also called idiopathic pulmonary fibrosis (IPF), interstitial diffuse pulmonary fibrosis, inflammatory pulmonary fibrosis, or fibrosing alveolitis, is a lung disorder and a heterogeneous group of conditions characterized by abnormal formation of fibrous tissue between alveoli caused by alveolitis comprising cellular infiltration into the alveolar septae with resulting fibrosis. The effects of IPF are chronic, progressive, and often fatal.

The clinical course of IPF is variable and largely unpredictable. IPF is ultimately fatal, with historical data suggesting a median survival time of 2-3 years from diagnosis. A decline in forced vital capacity (FVC) is indicative of disease progression in patients with IPF and change in FVC is the most commonly used endpoint in clinical trials. A decline in FVC of 5% or 10% of the predicted value over 6-12 months has been associated with increased mortality in patients with IPF.

Our understanding of the pathogenesis of IPF has evolved from that of a predominantly inflammatory disease to one driven by a complex interplay of repeated epithelial cell damage and aberrant wound healing, involving fibroblast recruitment, proliferation and differentiation, and culminating in excess deposition of extracellular matrix. This shift in knowledge prompted a change in the type of compounds being investigated as potential therapies, with those targeted at specific pathways in the development and progression of fibrosis becoming the focus.

In patients with IPF, the mechanisms whereby PI3K/mTOR inhibitors act may involve inhibition of kinases such as PI3Ks and mTOR. This results in inactivation of cellular receptors for mediators involved in the development of pulmonary fibrosis. As a result, fibroblast proliferation is inhibited and extracellular matrix deposition is reduced. ("Update on diagnosis and treatment of idiopathic pulmonary fibrosis", *J Bras Pneumol.* 2015, 41 (5), 454-466.)

Accordingly, small-molecule compounds that specially inhibit, regulate and/or modulate the signal transduction of kinases, particularly including PI3K and mTOR as described above, are desirable as a means to prevent, manage, or treat proliferative disorders and fibrosis, particular idiopathic pulmonary fibrosis in a patient. One such small-molecule is N-(5-(3-cyanopyrazolo[1,5-α]pyridin-5-yl)-2-methoxypyridin-3-yl)-2,4-difluorobenzenesulfonamide, which has the chemical structure as shown in the following:

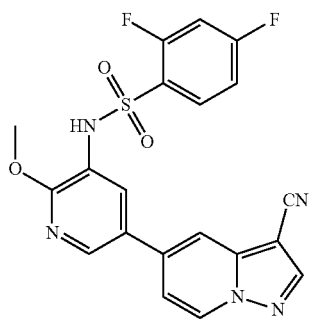 [SMILES: COc1ncc(-c2ccn3ncc(C#N)c3c2)cc1NS(=O)(=O)c1ccc(F)cc1F]

WO 2014130375A1 described the synthesis of N-(5-(3-cyanopyrazolo[1,5-α]pyridin-5-yl)-2-methoxypyridin-3-yl)-2,4-difluorobenzenesulfonamide (Example 3) and also disclosed the therapeutic activity of this molecule in inhibiting, regulating and modulating the signal transduction of protein kinases.

Different salts and solid state forms of an active pharmaceutical ingredient may possess different properties. Such variations in the properties of different salts and solid state forms may provide a basis for improving formulation, for example, by facilitating better processing or handling characteristics, improving the dissolution profile, stability (polymorph as well as chemical stability) and shelf-life. These variations in the properties of different salts and solid state forms may also provide improvements to the final dosage form, for example, if they serve to improve bioavailability. Different salts and solid state forms of an active pharmaceutical ingredient may also give rise to a variety of polymorphs or crystalline forms, which may in turn provide additional opportunities to assess variations in the properties and characteristics of a solid active pharmaceutical ingredient.

Different salts and solid state forms of N-(5-(3-cyanopyrazolo[1,5-α]pyridin-5-yl)-2-methoxypyridin-3-yl)-2,4-difluorobenzenesulfonamide are described herein.

SUMMARY OF THE INVENTION

The present invention provides base addition salts of compound of formula (I) that inhibit, regulate, and/or modulate PI3K and/or mTOR, and are useful in the treatment of hyperproliferative diseases, such as cancer, in humans. This invention also provides methods for preparing the salts. Base addition salts in the present invention can be crystalline forms, partly crystalline forms, polymorphs or amorphous form. The base addition salts of this invention can also be solvates, such as hydrate.

In one aspect, provided herein is a pharmaceutically acceptable base addition salt of a compound of Formula (I),

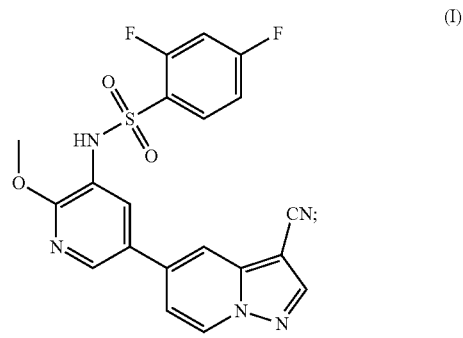

wherein, the base addition salt is a sodium salt, a lithium salt, a potassium salt, a choline salt, a calcium salt, a magnesium salt, an amine salt, a lysinate, an arginine salt, an ethanolamine salt, a tromethamine salt, a N-methylglucosamine salt, a morpholine salt, a piperazine salt, a tert-butylamine salt, a dicyclohexyl amine salt or a combination thereof.

In other embodiments, the sodium salt is a mono-sodium salt of compound of formula (I).

In some embodiments, the mono-sodium salt is crystalline form A of mono-sodium salt of compound of formula (I) having an X-ray powder diffraction pattern comprising 2θ values at 14.73°±0.2°, 14.93°±0.2°, 21.77°±0.2°, 22.59°±0.2°, 23.29°±0.2° and 24.87°±0.2°.

In other embodiments, the mono-sodium salt is crystalline form A of mono-sodium salt of compound of formula (I) having an X-ray powder diffraction pattern comprising 2θ values at 10.71°±0.2°, 14.73°±0.2°, 14.93°±0.2°, 19.01°±0.2°, 19.41°±0.2°, 21.57°±0.2°, 21.77°±0.2°, 22.59°±0.2°, 23.29°±0.2°, 24.87°±0.2°, 28.36°±0.2° and 30.18°±0.2°.

In some embodiments, the mono-sodium salt is crystalline form A of mono-sodium salt of compound of formula (I) having an X-ray powder diffraction pattern comprising 2θ values at 5.59°±0.2°, 9.33°±0.2°, 10.71°±0.2°, 11.21°±0.2°, 14.73°±0.2°, 14.93°±0.2°, 15.39°±0.2°, 16.55°±0.2°, 17.36°±0.2°, 17.64°±0.2°, 18.42°±0.2°, 19.01°±0.2°, 19.41°±0.2°, 19.66°±0.2°, 19.84°±0.2°, 20.26°±0.2°, 21.57°±0.2°, 21.77°±0.2°, 22.34°±0.2°, 22.59°±0.2°, 23.29°±0.2°, 24.15°±0.2°, 24.87°±0.2°, 25.59°±0.2°, 26.26°±0.2°, 26.75°±0.2°, 27.32°±0.2°, 27.87°±0.2°, 28.36°±0.2°, 28.71°±0.2°, 29.08°±0.2°, 29.59°±0.2°, 30.18°±0.2°, 30.56°±0.2°, 31.01°±0.2°, 31.61°±0.2°, 31.81°±0.2°, 32.14°±0.2°, 32.72°±0.2°, 33.26°±0.2°, 34.14°±0.2°, 35.97°±0.2°, 36.46°±0.2°, 38.40°±0.2°, 38.83°±0.2°, 39.49°±0.2°, 40.04°±0.2°, 41.32°±0.2°, 42.80°±0.2°, 43.89°±0.2° and 45.77°±0.2°.

In some embodiments, the mono-sodium salt is crystalline form A of mono-sodium salt of compound of formula (I) having an X-ray powder diffraction (XRPD) pattern substantially in accordance with the pattern shown in FIG. 1.

In some embodiments, the mono-sodium salt is crystalline form B of mono-sodium salt of compound of formula (I) having an X-ray powder diffraction pattern comprising 2θ values at 8.75°±0.2°, 12.27°±0.2°, 14.42°±0.2°, 20.46°±0.2°, 23.64°±0.2°, 25.14°±0.2° and 25.89°±0.2°.

In other embodiments, the mono-sodium salt is crystalline form B of mono-sodium salt of compound of formula (I) having an X-ray powder diffraction pattern comprising 2θ values at 8.75°±0.2°, 12.27°±0.2°, 14.42°±0.2°, 15.62°±0.2°, 20.46°±0.2°, 23.32°±0.2°, 23.64°±0.2°, 25.14°±0.2°, 25.89°±0.2°, 26.87°±0.2°, 27.43°±0.2°, 28.09°±0.2°, 32.95°±0.2° and 36.47°±0.2°.

In some embodiments, the mono-sodium salt is crystalline form B of mono-sodium salt of compound of formula (I) having an X-ray powder diffraction pattern comprising 2θ values at 7.23°±0.2°, 8.75°±0.2°, 12.27°±0.2°, 12.88°±0.2°, 13.94°±0.2°, 14.42°±0.2°, 14.87°±0.2°, 15.62°±0.2°, 17.85°±0.2°, 18.51°±0.2°, 18.94°±0.2°, 19.33°±0.2°, 19.79°±0.2°, 20.46°±0.2°, 21.50°±0.2°, 22.23°±0.2°, 22.79°±0.2°, 23.32°±0.2°, 23.64°±0.2°, 24.67°±0.2°, 25.14°±0.2°, 25.89°±0.2°, 26.87°±0.2°, 27.43°±0.2°, 28.09°±0.2°, 28.54°±0.2°, 29.02°±0.2°, 29.48°±0.2°, 29.96°±0.2°, 30.74°±0.2°, 31.56°±0.2°, 32.95°±0.2°, 33.50°±0.2°, 35.86°±0.2°, 36.47°±0.2°, 37.32°±0.2°, 39.11°±0.2°, 39.84°±0.2°, 42.23°±0.2°, 42.93°±0.2° and 44.44°±0.2°.

In other embodiments, the mono-sodium salt is crystalline form B of mono-sodium salt of compound of formula (I) having an X-ray powder diffraction (XRPD) pattern substantially in accordance with the pattern shown in FIG. 2.

In some embodiments, the mono-sodium salt is crystalline form C of mono-sodium salt of compound of formula (I) having an X-ray powder diffraction pattern comprising 2θ values at 10.52°±0.2°, 13.64°±0.2°, 14.40°±0.2°, 15.86°±0.2°, 18.72°±0.2°, 19.14°±0.2° and 24.68°±0.2°.

In other embodiments, the mono-sodium salt is crystalline form C of mono-sodium salt of compound of formula (I) having an X-ray powder diffraction pattern comprising 2θ values at 10.52°±0.2°, 13.64°±0.2°, 14.40°±0.2°, 15.86°±0.2°, 18.72°±0.2°, 19.14°±0.2°, 19.47°±0.2°, 20.31°±0.2°, 21.16°±0.2°, 23.94°±0.2°, 24.68°±0.2°, 26.21°±0.2° and 29.03°±0.2°.

In other embodiments, the mono-sodium salt is crystalline form C of mono-sodium salt of compound of formula (I) having an X-ray powder diffraction pattern comprising 2θ values at 5.24°±0.2°, 5.61°±0.2°, 8.88°±0.2°, 9.54°±0.2°, 10.52°±0.2°, 13.64°±0.2°, 14.40°±0.2°, 14.78°±0.2°, 15.86°±0.2°, 16.46°±0.2°, 16.95°±0.2°, 17.86°±0.2°, 18.72°±0.2°, 19.14°±0.2°, 19.47°±0.2°, 20.31°±0.2°, 20.74°±0.2°, 21.16°±0.2°, 22.09°±0.2°, 22.61°±0.2°, 23.94°±0.2°, 24.29°±0.2°, 24.68°±0.2°, 26.21°±0.2°, 27.03°±0.2°, 27.60°±0.2°, 28.32°±0.2°, 29.03°±0.2°, 30.10°±0.2°, 31.73°±0.2°, 31.94°±0.2°, 33.86°±0.2°, 34.33°±0.2°, 35.60°±0.2°, 36.01°±0.2°, 36.95°±0.2°, 38.02°±0.2°, 38.86°±0.2°, 40.32°±0.2°, 41.00°±0.2°, 42.08°±0.2° and 44.21°±0.2°.

In other embodiments, the mono-sodium salt is crystalline form C of mono-sodium salt of compound of formula (I) having an X-ray powder diffraction (XRPD) pattern substantially in accordance with the pattern shown in FIG. 3.

In some embodiments, the mono-sodium salt is an amorphous form of mono-sodium salt of compound of formula (I) having an X-ray powder diffraction (XRPD) pattern substantially in accordance with the pattern shown in FIG. 4.

In some embodiments, the lithium salt is crystalline form A of mono-lithium salt of compound of formula (I) having an X-ray powder diffraction pattern comprising 2θ values at 9.98°±0.2°, 13.82°±0.2°, 21.74°±0.2°, 23.70°±0.2°, 25.03°±0.2°, 26.82°±0.2° and 32.96°±0.2°.

In other embodiments, the lithium salt is crystalline form A of mono-lithium salt of compound of formula (I) having an X-ray powder diffraction pattern comprising 2θ values at 9.98°±0.2°, 13.82°±0.2°, 15.83°±0.2°, 16.25°±0.2°, 19.64°±0.2°, 20.02°±0.2°, 21.74°±0.2°, 22.16°±0.2°, 23.70°±0.2°, 25.03°±0.2°, 26.38°±0.2°, 26.82°±0.2°, 30.27°±0.2° and 32.96°±0.2°.

In other embodiments, the lithium salt is crystalline form A of mono-lithium salt of compound of formula (I) having an X-ray powder diffraction pattern comprising 2θ values at 3.60°±0.2°, 8.33°±0.2°, 8.97°±0.2°, 9.58°±0.2°, 9.98°±0.2°, 11.25°±0.2°, 12.24°±0.2°, 13.26°±0.2°, 13.82°±0.2°, 15.34°±0.2°, 15.83°±0.2°, 16.25°±0.2°, 16.61°±0.2°, 17.31°±0.2°, 18.06°±0.2°, 18.90°±0.2°, 19.64°±0.2°, 20.02°±0.2°, 21.02°±0.2°, 21.28°±0.2°, 21.74°±0.2°, 22.16°±0.2°, 23.70°±0.2°, 24.37°±0.2°, 25.03°±0.2°, 25.52°±0.2°, 26.38°±0.2°, 26.82°±0.2°, 27.59°±0.2°, 28.15°±0.2°, 28.74°±0.2°, 29.30°±0.2°, 29.69°±0.2°, 30.27°±0.2°, 30.82°±0.2°, 31.45°±0.2°, 32.60°±0.2°, 32.96°±0.2°, 33.96°±0.2°, 36.26°±0.2°, 37.86°±0.2°, 38.76°±0.2°, 39.40°±0.2°, 41.02°±0.2°, 41.98°±0.2°, 42.73°±0.2° and 43.64°±0.2°.

In other embodiments, the lithium salt is crystalline form A of mono-lithium salt of compound of formula (I) having an X-ray powder diffraction (XRPD) pattern substantially in accordance with the pattern shown in FIG. 5.

In some embodiments, the potassium salt is crystalline form A of mono-potassium salt of compound of formula (I) having an X-ray powder diffraction pattern comprising 2θ values at 11.04°±0.2°, 16.29°±0.2°, 19.75°±0.2°, 21.26°±0.2°, 22.22°±0.2° and 23.33°±0.2°.

In other embodiments, the potassium salt is crystalline form A of mono-potassium salt of compound of formula (I) having an X-ray powder diffraction pattern comprising 2θ values at 11.04°±0.2°, 14.28°±0.2°, 16.29°±0.2°, 19.75°±0.2°, 20.01°±0.2°, 21.26°±0.2°, 22.22°±0.2°, 23.33°±0.2°, 24.02°±0.2°, 25.87°±0.2°, 27.83°±0.2° and 32.47°±0.2°.

In other embodiments, the potassium salt is crystalline form A of mono-potassium salt of compound of formula (I) having an X-ray powder diffraction pattern comprising 2θ values at 5.53°±0.2°, 11.04°±0.2°, 14.28°±0.2°, 14.67°±0.2°, 16.29°±0.2°, 17.19°±0.2°, 19.18°±0.2°, 19.75°±0.2°, 20.01°±0.2°, 21.26°±0.2°, 21.61°±0.2°, 22.22°±0.2°, 23.33°±0.2°, 24.02°±0.2°, 25.47°±0.2°, 25.87°±0.2°, 26.46°±0.2°, 27.07°±0.2°, 27.83°±0.2°, 28.76°±0.2°, 29.49°±0.2°, 30.37°±0.2°, 31.01°±0.2°, 32.47°±0.2°, 32.96°±0.2°, 33.64°±0.2°, 33.98°±0.2°, 36.27°±0.2°, 38.87°±0.2°, 39.22°±0.2°, 40.59°±0.2°, 41.36°±0.2°, 41.77°±0.2°, 43.03°±0.2°, 44.51°±0.2°, 46.39°±0.2°, 47.48°±0.2°, 48.26°±0.2°, 50.58°±0.2°, 51.71°±0.2° and 54.23°±0.2°.

In other embodiments, the potassium salt is crystalline form A of mono-potassium salt of compound of formula (I), wherein said crystalline form A of mono-potassium salt is characterized by an X-ray powder diffraction (XRPD) pattern substantially in accordance with the pattern shown in FIG. 6.

In some embodiments, the choline salt is crystalline form A of mono-choline salt of compound of formula (I) having an X-ray powder diffraction pattern comprising 2θ values at 8.31°±0.2°, 16.94°±0.2°, 19.82°±0.2°, 22.20°±0.2°, 22.63°±0.2° and 22.85°±0.2°.

In other embodiments, the choline salt is crystalline form A of mono-choline salt of compound of formula (I) having an X-ray powder diffraction pattern comprising 2θ values at 5.65°±0.2°, 8.31°±0.2°, 10.31°±0.2°, 16.53°±0.2°, 16.94°±0.2°, 17.27°±0.2°, 19.82°±0.2°, 22.20°±0.2°, 22.63°±0.2°, 22.85°±0.2°, 23.97°±0.2°, 24.81°±0.2° and 29.07°±0.2°.

In other embodiments, the choline salt is crystalline form A of mono-choline salt of compound of formula (I) having an X-ray powder diffraction pattern comprising 2θ values at 5.65°±0.2°, 7.12°±0.2°, 7.52°±0.2°, 8.31°±0.2°, 9.40°±0.2°, 10.31°±0.2°, 11.29°±0.2°, 13.51°±0.2°, 14.92°±0.2°, 15.29°±0.2°, 16.53°±0.2°, 16.94°±0.2°, 17.27°±0.2°, 17.50°±0.2°, 18.80°±0.2°, 19.82°±0.2°, 22.20°±0.2°, 22.63°±0.2°, 22.85°±0.2°, 23.42°±0.2°, 23.97°±0.2°, 24.39°±0.2°, 24.81°±0.2°, 25.11°±0.2°, 25.45°±0.2°, 26.19°±0.2°, 26.95°±0.2°, 27.70°±0.2°, 28.52°±0.2°, 29.07°±0.2°, 30.15°±0.2°, 31.21°±0.2°, 32.12°±0.2°, 32.95°±0.2°, 33.33°±0.2°, 34.15°±0.2°, 35.49°±0.2°, 36.11°±0.2°, 38.57°±0.2°, 40.18°±0.2°, 41.92°±0.2° and 42.99°±0.2°.

In other embodiments, the choline salt is crystalline form A of mono-choline salt of compound of formula (I) having an X-ray powder diffraction (XRPD) pattern substantially in accordance with the pattern shown in FIG. 7.

In another aspect, provided herein is a pharmaceutical composition comprising a base addition salt disclosed herein, and a pharmaceutically acceptable carrier, excipient, diluents, adjuvant, or a combination thereof.

In some embodiments, the pharmaceutical composition disclosed herein further comprises an additional therapeutic agent selected from a chemotherapeutic agent, an anti-proliferative agent, an agent for treating atherosclerosis, an agent for treating lung fibrosis or a combination thereof.

In some embodiments, the base addition salt in the pharmaceutical composition disclosed herein can be one of any solid state forms, specifically one of any crystalline forms, amorphous form or a combination thereof.

In further embodiments, the additional therapeutic agent is chlorambucil, melphalan, cyclophosphamide, ifosfamide, busulfan, carmustine, lomustine, streptozocin, cisplatin, carboplatin, oxaliplatin, dacarbazine, temozolomide, procarbazine, methotrexate, fluorouracil, cytarabine, gemcitabine, mercaptopurine, fludarabine, vinblastine, vincristine, vinorelbine, paclitaxel, docetaxel, topotecan, irinotecan, etoposide, trabectedin, dactinomycin, doxorubicin, epirubicin, daunorubicin, mitoxantrone, bleomycin, mitomycin, ixabepilone, tamoxifen, flutamide, gonadorelin analogues, megestrol, prednidone, dexamethasone, methylprednisolone, thalidomide, interferon alfa, leucovorin, sirolimus, temsirolimus, everolimus, afatinib, alisertib, amuvatinib, apatinib, axitinib, bortezomib, bosutinib, brivanib, cabozantinib, cediranib, crenolanib, crizotinib, dabrafenib, dacomitinib, danusertib, dasatinib, erlotinib, ganetespib, gefitinib, ibrutinib, icotinib, imatinib, iniparib, lapatinib, lenvatinib, lmasitinib, neratinib, nilotinib, niraparib, oprozomib, olaparib, pazopanib, ponatinib, quizartinib, regorafenib, rigosertib, rucaparib, ruxolitinib, saracatinib, saridegib, sorafenib, sunitinib, tasocitinib, telatinib, tivozanib, tofacitinib, trametinib, vandetanib, veliparib, vemurafenib, vismodegib, alemtuzumab, bevacizumab, brentuximab vedotin, catumaxomab, cetuximab, denosumab, gemtuzumab, ipilimumab, nimotuzumab, ofatumumab, panitumumab, ramucirumab, rituximab, trastuzumab, or a combination thereof.

In another aspect, provided herein is a method for preventing, managing, treating or lessening the severity of a proliferative disorder in a patient infected with the proliferative disorder, which comprises administrating a pharmaceutically effective amount of the base addition salt disclosed herein, or the pharmaceutical composition disclosed herein to the patient.

In another aspect, provided herein is use of the base addition salt and its pharmaceutical composition disclosed herein in the manufacture of a medicament for preventing, managing, treating or lessening the severity of a proliferative disorder in a patient.

In some embodiments, the proliferative disorder is metastatic cancer, colon cancer, gastric adenocarcinoma, bladder cancer, breast cancer, kidney cancer, liver cancer, lung cancer, skin cancer, thyroid cancer, cancer of the head and neck, prostate cancer, pancreatic cancer, cancer of the CNS, glioblastoma, a myeloproliferative disorder, atherosclerosis or lung fibrosis.

In another aspect, provided herein is use of the base addition salt and its pharmaceutical composition disclosed herein the manufacture of a medicament for inhibiting or modulating protein kinase.

In some embodiments, the protein kinase is PI3K, mTOR or a combination thereof.

In some embodiments, provided herein is a method of inhibiting or modulating PI3K or mTOR, the method comprising contacting the kinase with the base addition salt according to the present invention, or with the composition according to the present invention. In some embodiments, the invention provides a method of inhibiting or modulating PI3K or mTOR signaling, the method comprising contacting the receptor with the base addition salt according to the present invention, or with the composition according to the present invention. In some embodiments, inhibition or modulation of PI3K or mTOR activity can be in a cell or a multicellular organism. If in a multicellular organism, the method according to this aspect of the invention comprises administering to the organism the base addition salt according to the present invention, or the composition according to the present invention. In some embodiments, the organism is a mammal. In other embodiments is a human. In still other embodiment, the method further comprises contacting the kinase with an additional therapeutic agent.

In another aspect, provided herein is a method of inhibiting proliferative activity of a cell, the method comprising contacting the cell with an effective proliferative inhibiting amount of a base addition salt according to the present invention or a composition thereof. In some embodiments, the method further comprises contacting the cell with an additional therapeutic agent.

In another aspect, provided herein is a method of treating a cell proliferative disease in a patient, the method comprising administering to the patient in need of such treatment an effective therapeutic amount of the base addition salt according to the present invention or the composition thereof. In some embodiments, the method further comprises administering an additional therapeutic agent.

In some embodiments, provided herein is a method of inhibiting tumor growth in a patient, the method comprising administering to the patient in need thereof an effective therapeutic amount of the base addition salt according to the present invention or the composition thereof. In some embodiments, the method further comprises administering an additional therapeutic agent.

In another aspect, provided herein is a method of preparing base addition salts of compound of formula (I).

The crystalline forms of base addition salt in this invention can be prepared by conventional preparation methods, and some crystalline forms can be prepared by means of crystalline transformation.

Amorphous form in this invention can be prepared by spray drying. The production rate of a spray drying as described in this invention is influenced by factors such as air inlet temperature, air outlet temperature and system pressure during the spray process. While air inlet temperature, air outlet temperature and system pressure during the spray process relates to the type of instrument and the solvent used.

The solvents used in the preparation of the salts in this invention are not specifically limited, and any solvents that can dissolve the starting material and not affect its nature are included in this invention. In addition, similar changes in the field, equivalent replacement, or equal to the present invention describes solvents, solvent combination, and the different proportion of solvent combination, are considered to be contained in the scope of the present invention. This invention presents the better solvents used in each reaction step.

The preparation of salts in this invention will be described in detail in the example part. Meanwhile, the present invention provides a biological test experiment for the salts (such as pharmacokinetic experiment), solubility experiment, stability experiment (including high temperature, high humidity and illumination experiment) and hygroscopicity experiment, etc. The results show that the salt has good biological activity, good solubility and high stability, and is suitable for pharmaceutical use.

DETAILED DESCRIPTION OF THE INVENTION

Definitions and General Terminology

Reference will now be made in detail to certain embodiments of the invention, examples of which are illustrated in the accompanying structures and formulas. The invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described herein. In the event that one or more of the incorporated literature, patents, and similar materials differs from or contradicts this application, including but not limited to defined terms, term usage, described techniques, or the like, this application controls.

Unless defined otherwise, all technical and scientific terms used herein have the same meaning as is commonly understood by one skilled in the art to which this invention belongs. All patents and publications referred to herein are incorporated by reference in their entirety.

The term "comprising" is meant to be open ended, including the indicated component but not excluding other elements.

The crystalline form is considered to be a graphical representation of the graph "described" in this invention. These include, for example, X-ray single crystal diffraction patterns, X-ray powder diffraction patterns, Raman spectroscopy, Fourier transform-infrared spectrum, DSC curve and solid NMR spectrum. Technicians will understand, minor errors can exist in this kind of data graphical representation (such as the relative peak intensity and peak position) because of changes of instrument response, sample concentration and purity which is well-known in this field. Nevertheless, the technicians can compare the graph data in this article with the graph data of the unknown crystalline form and confirm whether two sets of graph data represent the same crystalline form.

"XRD" refers to X-ray diffraction.

The term "amorphous" or "amorphous form" used in this invention is intended to represent that the substance, composition, or product, lacks a characteristic of crystalline form or crystalline structure. They are not crystalline forms when determined by XRPD, not birefringent or cube under polarized light microscopy or characterized by a diffused X-ray powder diffraction pattern with no sharp peaks. In some embodiments, samples containing the amorphous form of matter can be basically free of other amorphous forms and/or crystalline forms.

As used herein, a crystalline form that is "substantially pure" refers to a crystalline form that is substantially free of one or more other crystalline forms, i.e., the crystalline form has a purity of at least about 60%, at least about 70%, at least about 80%, at least about 85%, at least about 90%, at least about 93%, at least about 95%, at least about 98%, at least about 99%, at least about 99.5%, at least about 99.6%, at least about 99.7%, at least about 99.8%, or at least about 99.9%; or the crystalline form has less than 20%, less than 10%, less than 5%, less than 3%, less than 1%, less than 0.5%, less than 0.1%, or less than 0.01% of the one or more other crystalline forms and/or impurities, based on the total volume or weight of the crystalline form and the one or more other crystalline forms and/or impurities.

As used herein, an X-ray powder diffraction (XRPD) pattern or a differential scanning lorimetry (DSC) thermogram that is "substantially the same as shown" in a figure refers to an X-ray powder diffraction (XRPD) pattern, a differential scanning calorimetry (DSC) thermogram or a thermal gravimetric analysis curve (TGA) having at least 50%, at least 60%, at least 70%, at least 80%, at least 90%, at least 95%, or at least 99% of the peaks shown in the figure.

The term "2 theta value" or "2θ" refers to the peak position in degrees based on the experimental setup of the X-ray diffraction experiment and is a common abscissa unit in diffraction patterns. The experimental setup requires that if a reflection is diffracted when the incoming beam forms an angle theta (θ) with a certain lattice plane, the reflected beam is recorded at an angle 2 theta (2θ). It should be understood that reference herein to specific 2θ values for a specific polymorphic form is intended to mean the 2θ values (in degrees) as measured using the X-ray diffraction experimental conditions described herein. For example, as described in this invention, radiation source (Cu, kα, Kα1 (Å): 1.540598; Kα2 (Å): 1.544426; Kα2/Kα1 intensity ratio: 0.50) was used.

The term "X-ray powder diffraction pattern" or "XPRD pattern" or "XRD pattern" refers to the experimentally observed diffractogram or parameters derived therefrom. Powder X-ray diffraction patterns are characterized by peak position (abscissa) and intensities (ordinate). In the area of X-ray powder diffraction (XRD), relative peak height of XRD pattern depends on many factors related to sample preparation and geometric shapes of the instrument, while peak position is relatively insensitive to experimental details. Therefore, in some embodiments, the crystalline compounds described herein characterized by XRD pattern with some peak positions, have essentially the same characteristics as XRD pattern provided in appended drawings of the present invention. According to the current state of the instrument for the experiment, the error margin in the scattering angle (2θ) of the diffraction peaks is in the range of ±0.1°, ±0.2°, ±0.3°, ±0.4°, or ±0.5°. In some embodiments, the error margin is ±0.2°.

In the area of differential scanning calorimetry (DSC), relative peak height of DSC trace depends on many factors related to sample preparation and geometric shapes of the instrument, while peak position is relatively insensitive to experiment details. Therefore, in some embodiments, the crystalline compounds disclosed herein characterized by DSC trace with some peak positions, have essentially the same characteristics as DSC trace provided in appended drawings of the present invention. According to the current state of the instrument for the experiment, the error margin in the melting peaks is in the range of ±1° C., ±2° C., ±3° C., ±4° C., or ±5° C. In some embodiments, the error margin is ±3° C.

The term "relative intensity" refers to the intensity of a peak with respect to the intensity of the strongest peak in the X-ray powder diffraction pattern which is regarded as 100%.

As used herein, when referring to a spectrum and/or to data presented in a graph, the term "peak" refers to a feature that one skilled in the art would recognize as not attributable to background noise.

As used herein, all numbers disclosed herein are approximate values, regardless whether the word "about" is used in connection therewith. The value of each number may differ by 1%, 2%, 3%, 4%, 5%, 6%,7%, 8%,9%, 10%, 15% or 20%.

General Preparation Methods of Crystalline Forms

Crystalline forms may be prepared by a variety of methods including, but not limited to, for example, crystallization or recrystallization from a suitable solvent mixture; sublimation; growth from a melt; solid state transformation from another phase; crystallization from a supercritical fluid; and jet spraying. Techniques for crystallization or recrystallization of crystalline forms in a solvent mixture include, but are not limited to, for example, evaporation of the solvent; decreasing the temperature of the solvent mixture; crystal seeding of a supersaturated solvent mixture of the compound and/or salt thereof; freeze drying the solvent mixture; and adding anti-solvents (counter solvents) to the solvent mixture. High throughput crystallization techniques may be employed to prepare crystalline forms including polymorphs.

Crystals of drugs, including polymorphs, methods of preparation, and characterization of drug crystals are discussed in *Solid-State Chemistry of Drugs*, S. R. Byrn, R. R. Pfeiffer, and J. G. Stowell, 2$^{nd}$ Edition, SSCI, West Lafayette, Ind. (1999).

In a crystallization technique in which a solvent or solvents are employed, the solvent(s) are typically chosen based on one or more factors including, but not limited to, for example, solubility of the compound; crystallization technique utilized; and vapor pressure of the solvent. Combinations of solvents may be employed. For example, the compound may be solubilized in a first solvent to afford a solution, to which anti-solvent is then added to decrease the solubility of the compound in the solution, and precipitate to form crystals. An anti-solvent is a solvent in which a compound has low solubility.

Seed crystals may be added to any crystallization mixture to promote crystallization. Seeding may be employed to control growth of a particular polymorph and/or to control the particle size distribution of the crystalline product. Accordingly, calculation of the amount of seeds needed depends on the size of the seed available and the desired size of an average product particle as described, for example, in "Programmed Cooling Batch Crystallizers", J. W. Mullin and J. Nyvlt, *Chemical Engineering Science*, 1971, 26, 369-377. In general, seeds of small particle size are needed to effectively control the growth of crystals in the batch. Seeds of small particle size may be generated by sieving, milling or micronizing large crystals, or by microcrystallizing a solution. In the milling or micronizing of crystals, care should be taken to avoid changing crystallinity from the desired crystalline form (i.e., changing to an amorphous or other polymorphic form).

A cooled crystallization mixture may be filtered under vacuum and the isolated solid product may be washed with a suitable solvent, such as, for example, cold recrystallization solvent. After being washed, the product may be dried under a nitrogen or air purge to afford the desired crystalline form. The product may be analyzed by a suitable spectroscopic or analytical technique including, but not limited to, for example, differential scanning calorimetry (DSC); X-ray powder diffraction (XRD); and thermogravimetric analysis (TGA) to assure the crystalline form of the compound has been formed. The resulted crystalline form may be obtained in an amount greater than about 70 wt. % isolated yield, based on the weight of the compound originally employed in the crystallization procedure, and preferably greater than about 90 wt. % isolated yield.

X-ray powder diffraction Study (XRPD): The X-ray powder diffraction (XRPD) pattern was collected on an X-ray powder diffractometer (Empyrean, PANalytical, Holland) with an automatic transmission-reflection sample holder (3*15). The X-ray tube (Cu, kα, Kα1 (Å): 1.540598; Kα2 (Å): 1.544426; Kα2/Kα1=0.50) is set to voltage at 45 kV and current at 40 mA, irradiated length=10.0 mm. The scanning parameters were: continuous scan; range 3° to 40° (2θ±0.2°); step size 0.0168°; time per step 10 second. Data were collected at ambient temperature (from about 18 to about 30° C.). Sample (usually 1~2 mg) was prepared as flat plate specimens by slightly pressed on a glass slide to obtain a flat surface. The data were collected by Data Collector software, and analyzed by Data Viewer and HighScore Plus software.

Differential Scanning calorimetry (DSC) analysis: All DSC measurements were performed on a TA Instruments™ model Q2000 differential scanning calorimeter. The sample (about 2~6 mg) was weighted in an aluminum pan and recorded to a hundredth of a milligram, and transfer to the DSC instrument. The instrument was purged with nitrogen gas at 50 mL/min. Data were collected between room temperature and 300° C. at the heating rate of 10° C./min. The data was analyzed by TA Universal Analysis software.

Thermal Gravimetric Analyzer (TGA): All TGA scans were performed on TGA TA Q500 thermogravimetric analyzer. The sample (about 10~30 mg) was placed in a platinum pan pre-tared. The weight of the sample was measured accurately and recorded to a thousandth of a milligram by the instrument. The furnace was purged with nitrogen gas at 60 mL/min. Data were collected between room temperature and 300° C. at the hating rate of 10° C./min. The data was analyzed by TA Universal Analysis software.

$^1$H NMR spectra were recorded with a Bruker 400 MHz or 600 MHz spectrometer at ambient temperature. Solid-state $^{13}$C NMR spectra were recorded with a Bruker 100 MHz spectrometer at ambient temperature (from about 21° C. to about 25° C.) using TMS (0 ppm) as the reference standard. $^1$H NMR spectra were obtained as $CDCl_3$, DMSO-$d_6$, $CD_3OD$ or $d_6$-acetone solutions (reported in ppm), using TMS (0 ppm) or chloroform (7.25 ppm) as the reference standard. When peak multiplicities are reported, the following abbreviations are used: s (singlet), d (doublet), t (triplet), m (multiplet), br (broadened), dd (doublet of doublets), dt (doublet of triplets). Coupling constants J, when given, are reported in Hertz (Hz).

Low-resolution mass spectral (MS) data were generally determined on an Agilent 6120 Quadrupole HPLC-MS (Zorbax SB-C18, 2.1×30 mm, 3.5 micron, 6 minutes run, 0.6 mL/min flow rate, 5% to 95% (0.1% formic acid in $CH_3CN$) in (0.1% formic acid in $H_2O$)) with UV detection at 210 nm/254 nm and electrospray ionization mode (ESI).

Inductively coupled plasma mass spectrometry (ICP-MS) was used to analyze and determine the proportion of compound of formula (I) and inorganic base. Test condition: Agilent 7800 ICP-MS system, He model, Sc45 as the inner standard element.

DESCRIPTION OF THE PREFERRED EMBODIMENTS

Figure 1:
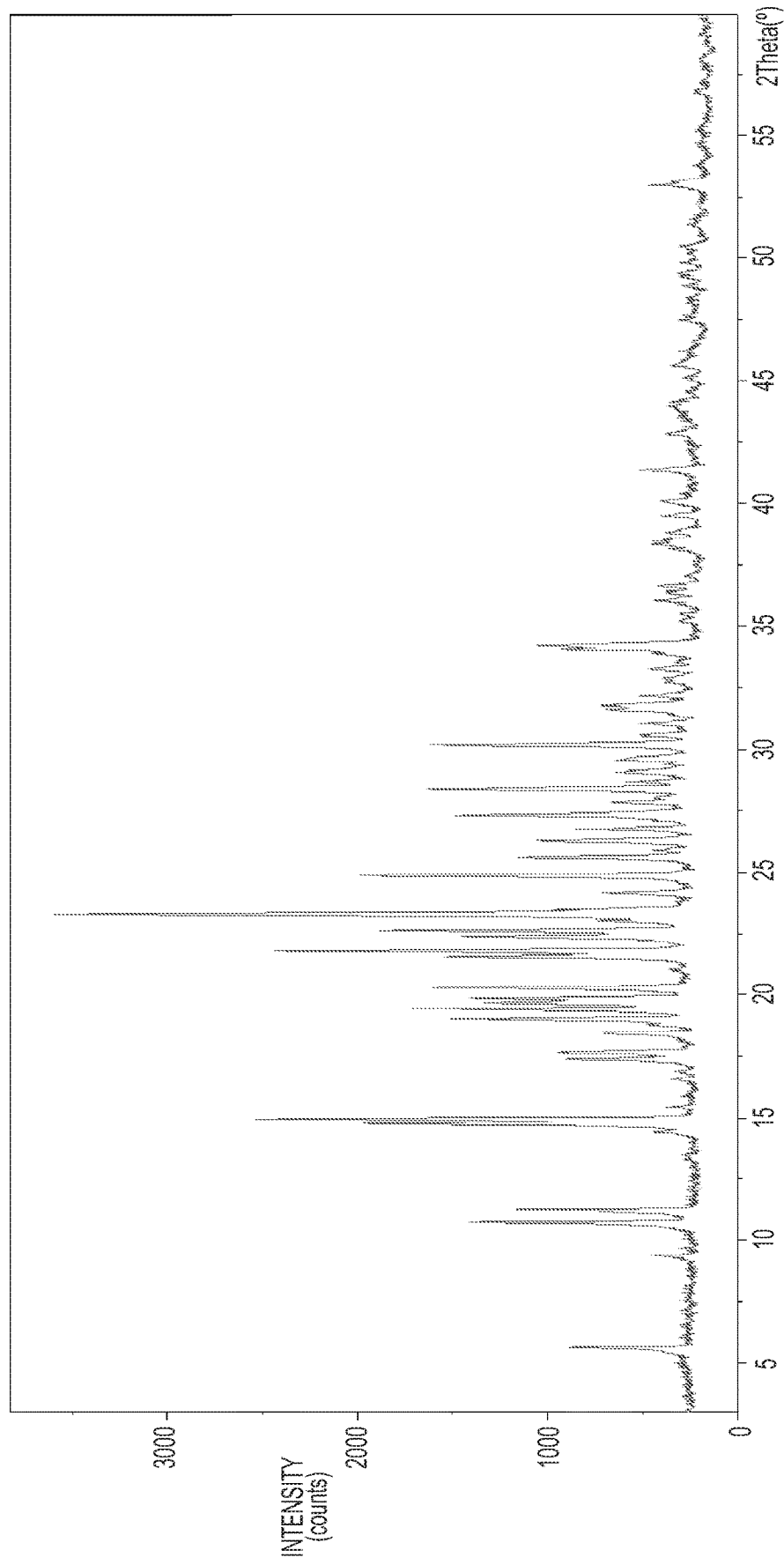
FIG. 1 depicts an X-ray powder diffraction pattern of the crystalline form A of mono-sodium salt of compound of formula (I).

The invention is further illustrated by the following examples, which are not be construed as limiting the invention in scope.

N-(5-(3-cyanopyrazolo[1,5-α]pyridin-5-yl)-2-methoxypyridin-3-yl)-2,4-difluorobenzenesulfonamide can be prepared according to the synthetic method of example 3 disclosed in WO2014130375 A1.

EXAMPLES

Example 1 Crystalline Form A of Mono-Sodium Salt of N-(5-(3-cyanopyrazolo[1,5-α]pyridin-5-yl)-2-methoxypyridin-3-yl)-2,4-difluorobenzenesulfonamide Method I for Preparation of Crystalline Form A of Mono-Sodium Salt To a mixture of N-(5-(3-cyanopyrazolo[1,5-α]pyridin-5-yl)-2-methoxypyridin-3-yl)-2,4-difluorobenzenesulfonamide (600.00 g, 1359 mmol) in acetone (5400 mL) was added a aqueous sodium hydroxide solution (59.81 g, 1495 mmol, 600 mL) at room temperature. The mixture was heated to 60±5° C. and stirred for 0.5 h, then cooled to 25±5° C. and filtered. The filtrate was added to the reaction kettle. The temperature was controlled at 25±5° C., and then isopropanol (12000 mL) was added. The mixture was cooled to 0±5° C. and stirred for 1 h, filtered to give the filter cake which was dried at 60° C. for 24 h to obtain the crude sodium salt. The mixture of the crude sodium salt in absolute ethanol (5500 mL) was heated to 78±5° C. and stirred for 4 h, then cooled to 0±5° C. and stirred for 1 h, filtered, the filter cake was dried at 60° C. for 24 h to obtain a light yellow solid (475 g, 86.4%).

Method II for Preparation of Crystalline Form A of Mono-Sodium Salt

To a mixture of N-(5-(3-cyanopyrazolo[1,5-α]pyridin-5-yl)-2-methoxypyridin-3-yl)-2,4-difluorobenzenesulfonamide (500 mg, 1.13 mmol) in ethanol (8 mL) was added a solution of sodium hydroxide (50 mg, 1.25 mmol) in ethanol (2 mL) at room temperature. The mixture was heated to 80±5° C. and stirred for 0.5 h, then cooled to 25±5° C. and filtered to give the filter cake which was dried at 60° C. for 24 h to obtain a yellow solid (446 mg, 84.97%).

Figure 8:
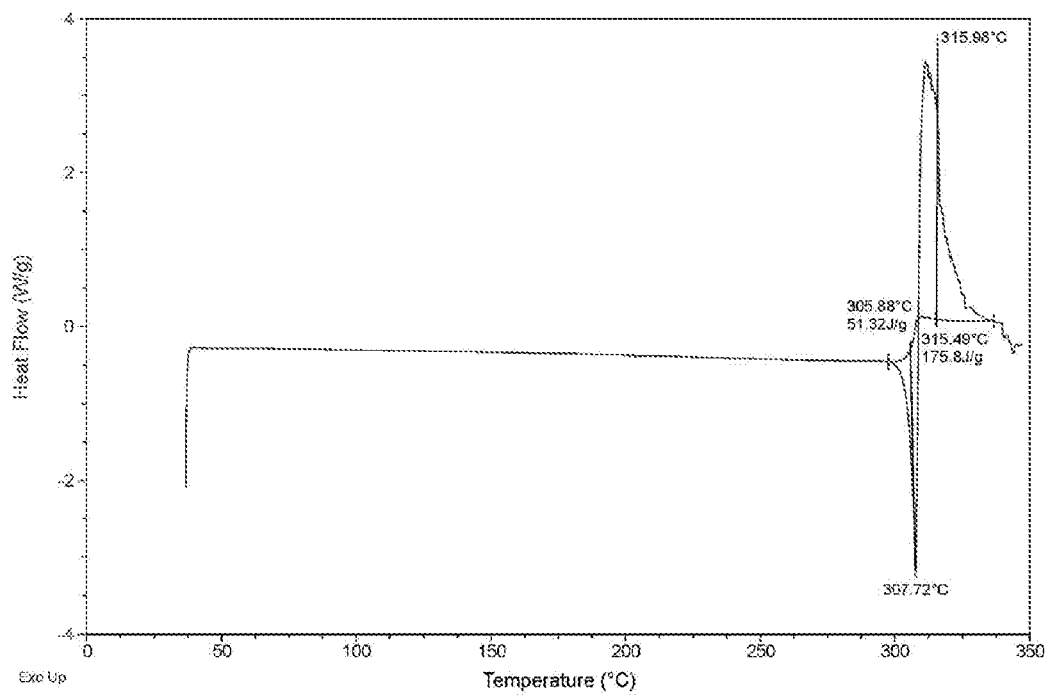
FIG. 8 depicts a differential scanning calorimetry thermogram of the crystalline form A of mono-sodium salt of compound of formula (I).

Identification of Crystalline Form A of Mono-Sodium Salt (1) The salt-forming ratio was 1:1 determined by ICP-MS.
(2) The X-ray powder diffraction pattern of crystalline form A of mono-sodium salt is shown in FIG. 1. The error margin in 2θ of the characteristic peaks was ±0.2°.
(3) The differential scanning calorimetry thermogram of crystalline form A of mono-sodium salt is shown in FIG. 8 which contains the endothermic peak of 307.72° C. The error margin was ±3° C.

Example 2 Crystalline Form B of Mono-Sodium Salt of N-(5-(3-cyanopyrazolo[1,5-α]pyridin-5-yl)-2-methoxypyridin-3-yl)-2,4-difluorobenzenesulfonamide

Preparation of Crystalline Form B of Mono-Sodium Salt

To a mixture of N-(5-(3-cyanopyrazolo[1,5-α]pyridin-5-yl)-2-methoxypyridin-3-yl)-2,4-difluorobenzenesulfonamide (2.00 g, 4.53 mmol) in acetone (40 mL) was added a aqueous sodium hydroxide solution (190 mg, 4.75 mmol, 2 mL) at room temperature. The mixture was heated to 60±5° C. and stirred for 0.5 h, then cooled to 25±5° C. and filtered. The temperature of the filtrate was controlled at 25±5° C. and then isopropanol (40 mL) was added. The mixture was stirred for 1 h and filtered to give the filter cake which was dried at 60° C. for 24 h to obtain a yellow solid (1.27 g, 60.5%).

Figure 2:
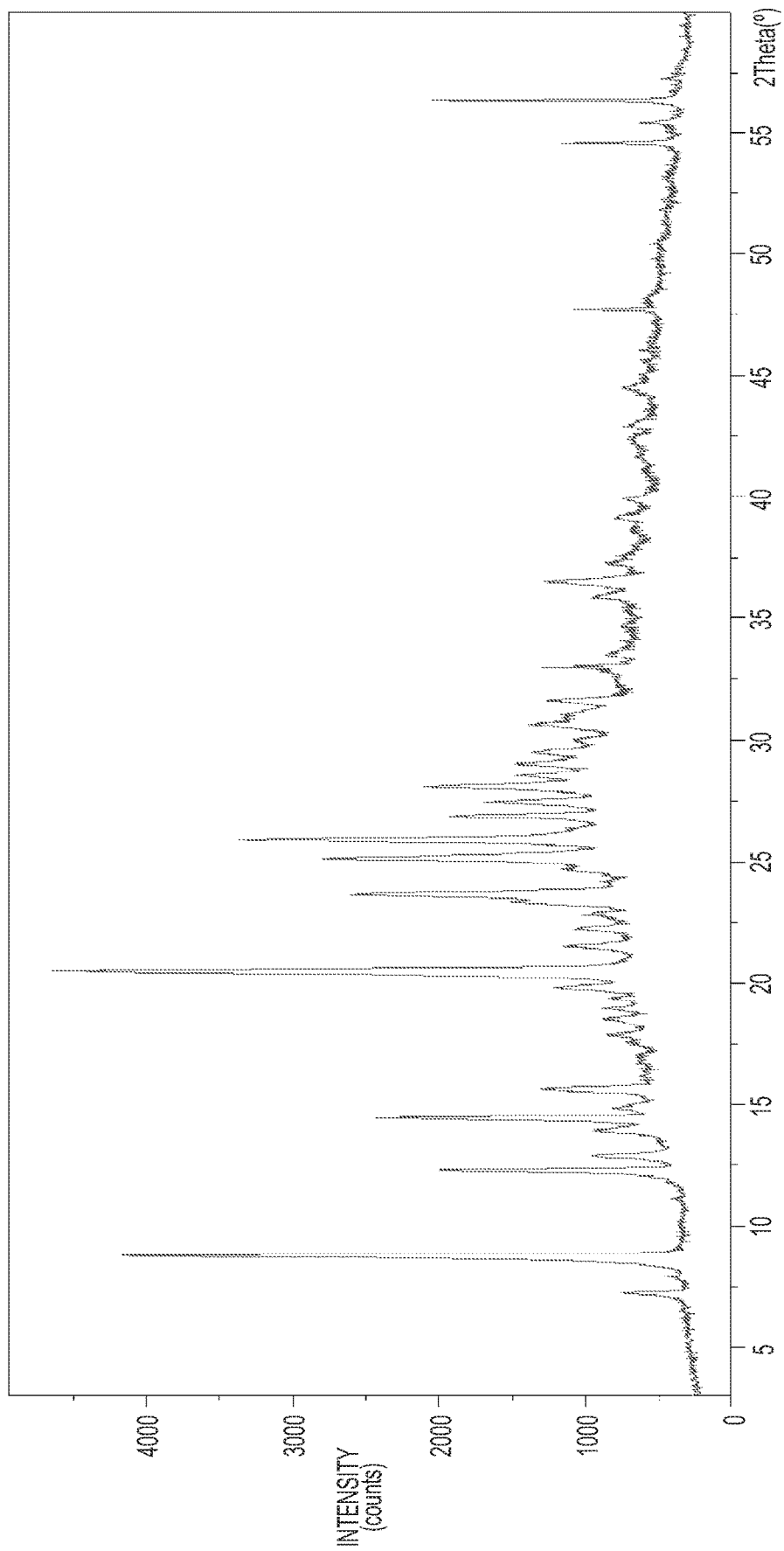
FIG. 2 depicts an X-ray powder diffraction pattern of the crystalline form B of mono-sodium salt of compound of formula (I).
Figure 9:
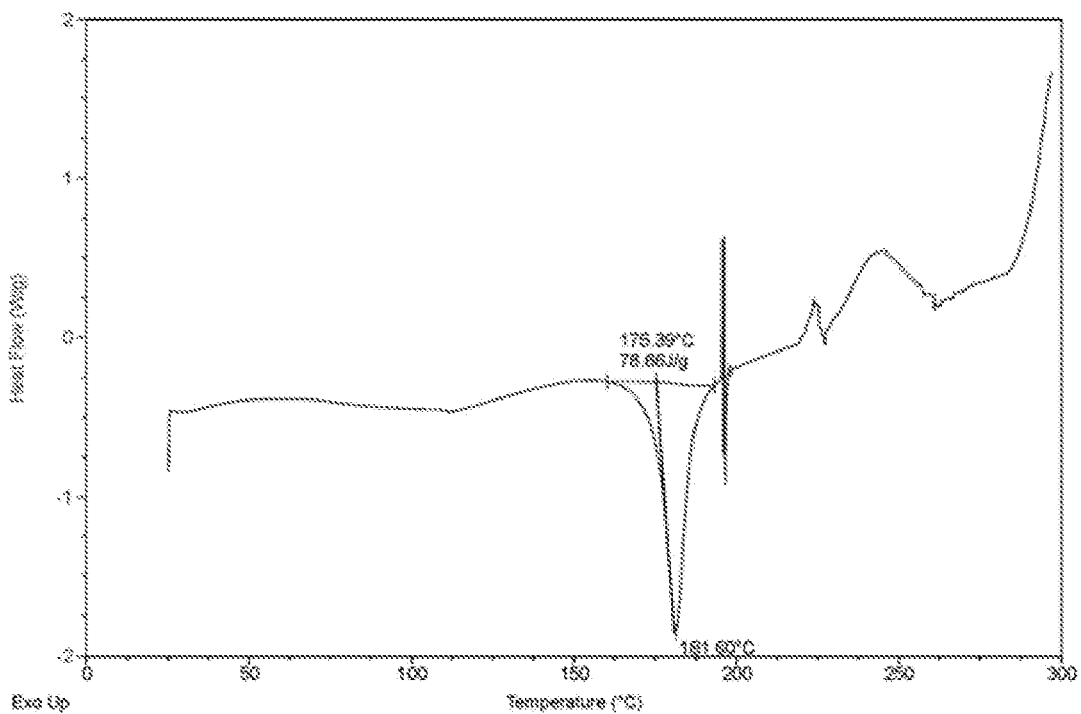
FIG. 9 depicts a differential scanning calorimetry thermogram of the crystalline form B of mono-sodium salt of compound of formula (I).

Identification of Crystalline Form B of Mono-Sodium Salt (1) The salt-forming ratio was 1:1 determined by ICP-MS.
(2) The X-ray powder diffraction pattern of crystalline form B of mono-sodium salt is shown in FIG. 2. The error margin in 2θ of the characteristic peaks was ±0.2°.
(3) The differential scanning calorimetry thermogram of crystalline form B of mono-sodium salt is shown in FIG. 9 which contains the endothermic peak of 181.60° C. The error margin was ±3° C.

Example 3 Crystalline Form C of Mono-Sodium Salt of N-(5-(3-cyanopyrazolo[1,5-α]pyridin-5-yl)-2-methoxypyridin-3-yl)-2,4-difluorobenzenesulfonamide

Preparation of Crystalline Form C of Mono-Sodium Salt

A mixture of sodium salt of N-(5-(3-cyanopyrazolo[1,5-α]pyridin-5-yl)-2-methoxypyridin-3-yl)-2,4-difluorobenzenesulfonamide (1.00 g, 2.16 mmol) in water (2 mL) and absolute ethanol (8 mL) was heated to reflux till the solid was completely dissolved, then cooled to 44° C. and filtered. The filter cake was dried at 60° C. for 24 h to obtain a light yellow solid (0.35 g, 35.0%).

Figure 3:
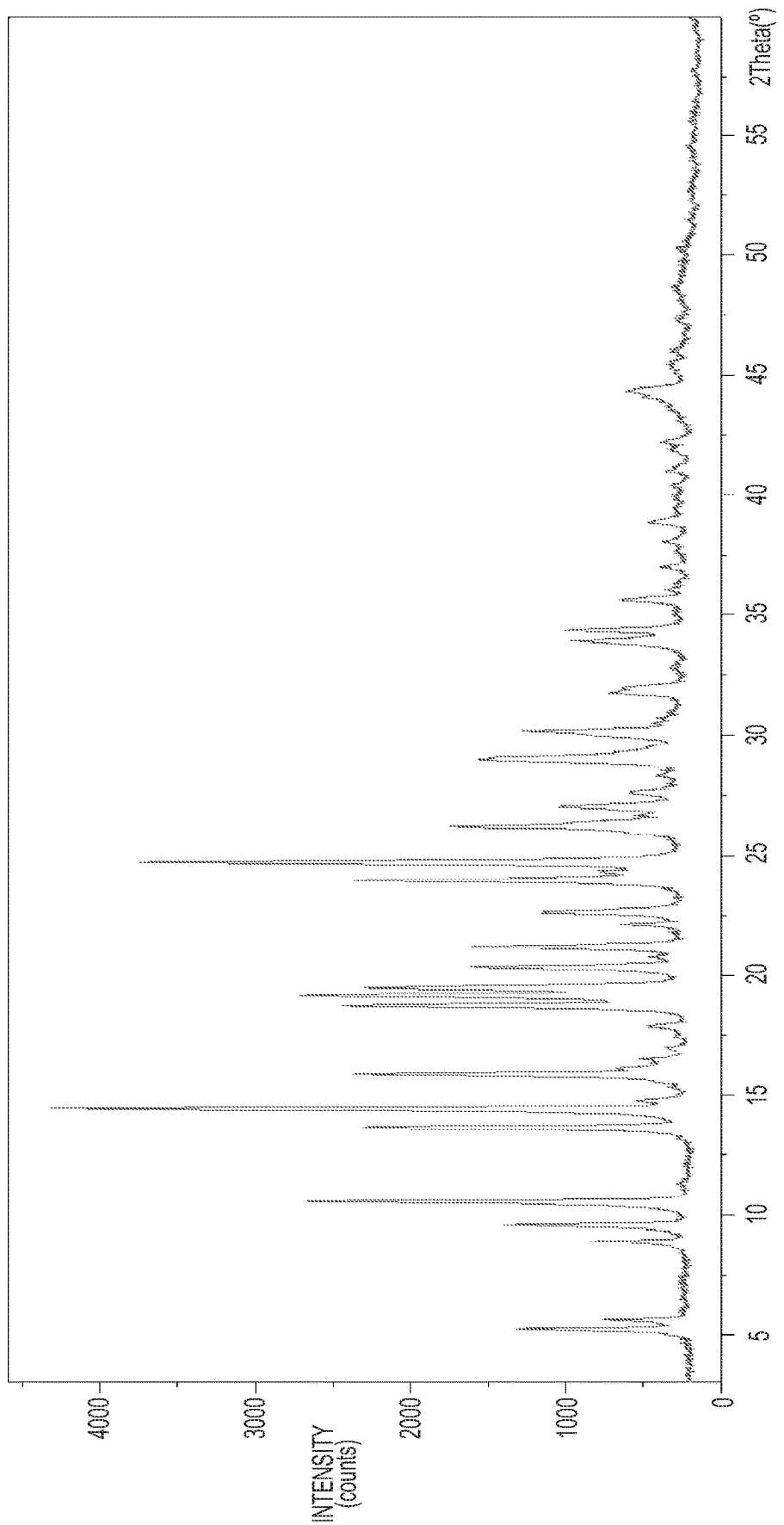
FIG. 3 depicts an X-ray powder diffraction pattern of the crystalline form C of mono-sodium salt of compound of formula (I).
Figure 10:
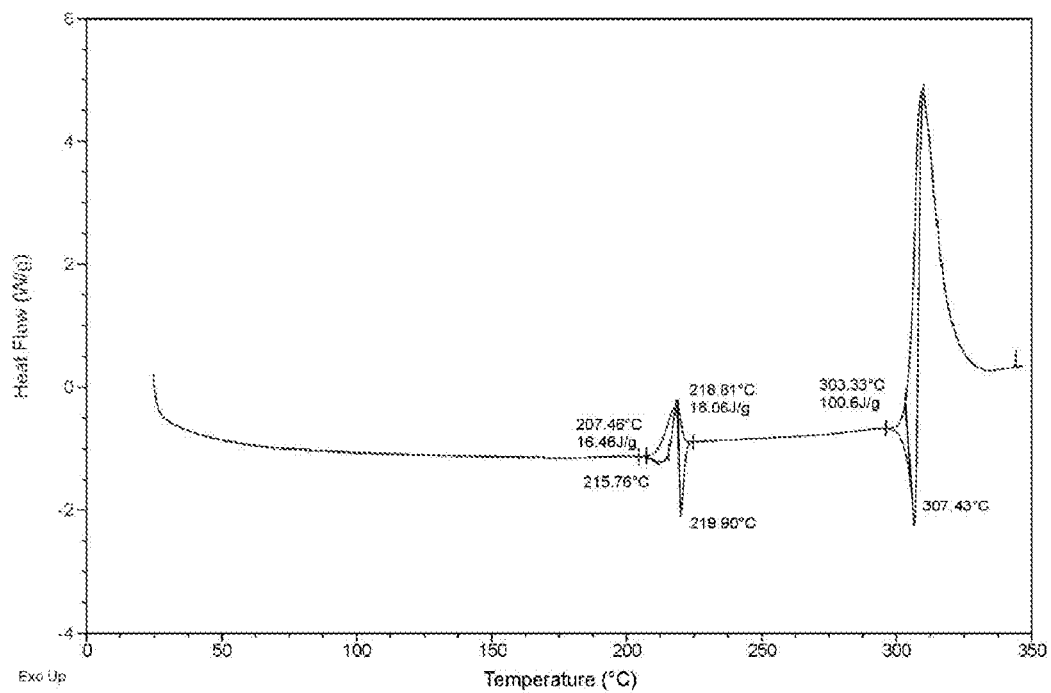
FIG. 10 depicts a differential scanning calorimetry thermogram of the crystalline form C of mono-sodium salt of compound of formula (I).

Identification of Crystalline Form C of Mono-Sodium Salt (1) The salt-forming ratio was 1:1 determined by ICP-MS.
(2) The X-ray powder diffraction pattern of crystalline form C of mono-sodium salt is shown in FIG. 3. The error margin in 2θ of the characteristic peaks was ±0.2°.
(3) The differential scanning calorimetry thermogram of crystalline form C of mono-sodium salt is shown in FIG. 10 which contains the endothermic peak of 215.76° C. The error margin was ±3° C.

Example 4 Amorphous Form of Mono-Sodium Salt of N-(5-(3-cyanopyrazolo[1,5-α]pyridin-5-yl)-2-methoxypyridin-3-yl)-2,4-difluorobenzenesulfonamide

Preparation of Amorphous Form of Mono-Sodium Salt

To a mixture of N-(5-(3-cyanopyrazolo[1,5-α]pyridin-5-yl)-2-methoxypyridin-3-yl)-2,4-difluorobenzenesulfonamide (1.00 g, 2.27 mmol) in dichloromethane (75 mL) and methanol (20 mL) was added a solution of sodium hydroxide (90 mg, 2.25 mmol) in methanol (5 mL) at room temperature. The mixture was heated to 80±5° C. and stirred for 0.5 h, then cooled to 25±5° C. and filtered. The filtrate was concentrated under reduced pressure to give a solid which was dried at 60° C. for 24 h to obtain a light yellow solid (1.05 g, 100%).

Figure 4:
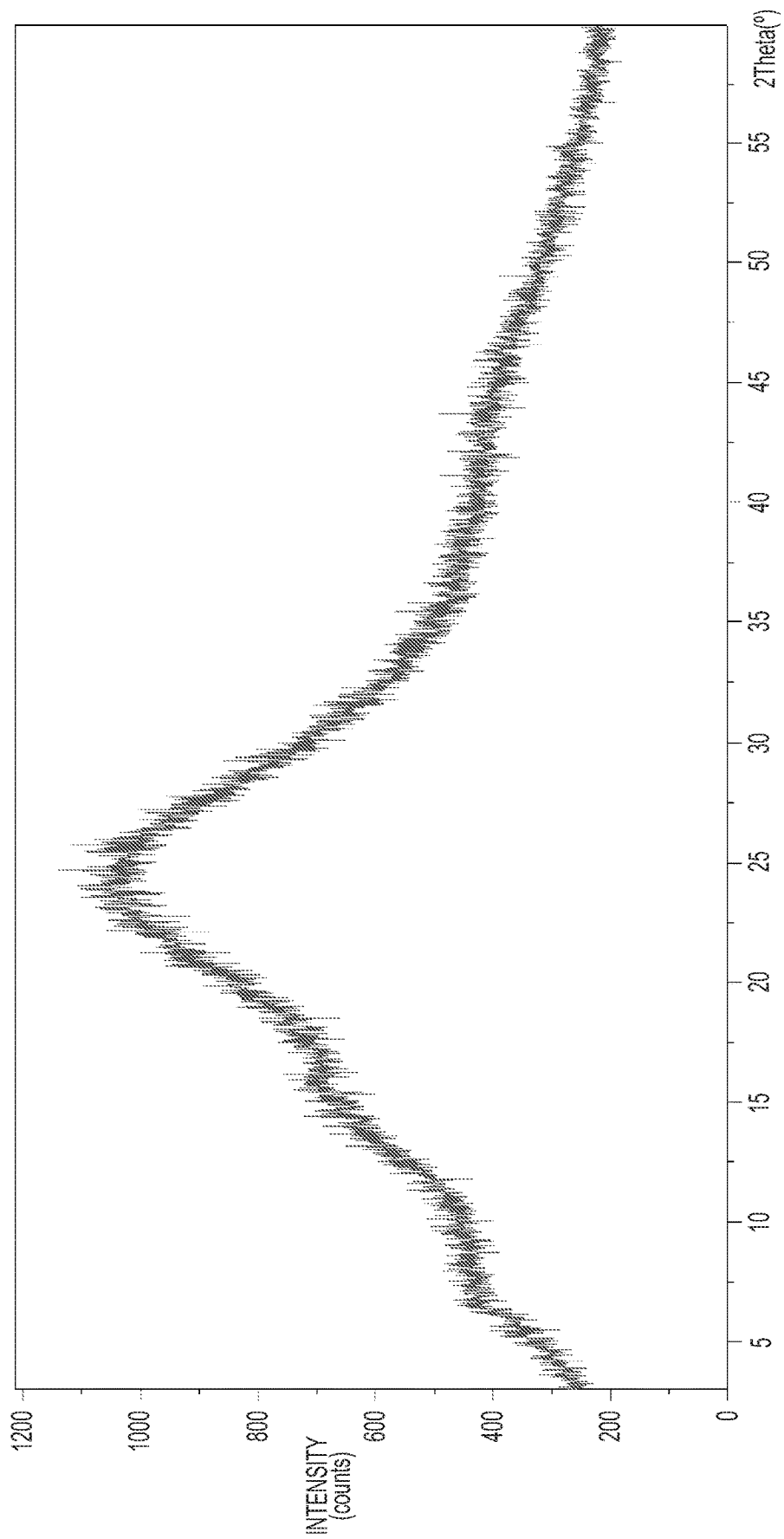
FIG. 4 depicts an X-ray powder diffraction pattern of the amorphous form of mono-sodium salt of compound of formula (I).
Figure 11:
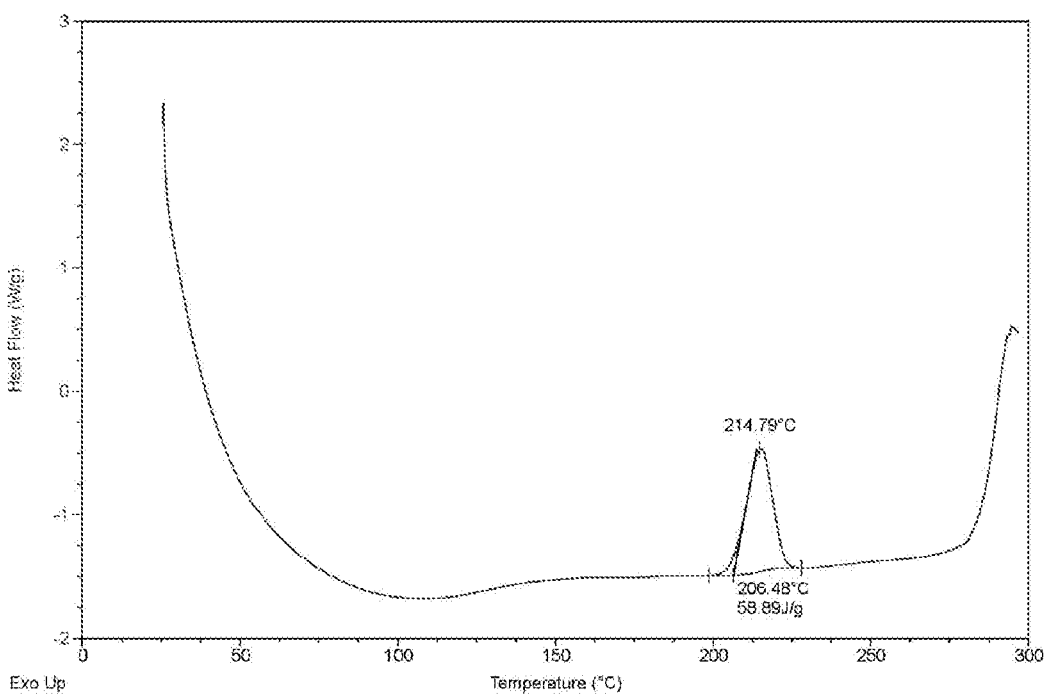
FIG. 11 depicts a differential scanning calorimetry thermogram of the amorphous form of mono-sodium salt of compound of formula (I).

Identification of Amorphous Form of Mono-Sodium Salt (1) The salt-forming ratio was 1:1 determined by ICP-MS.
(2) The X-ray powder diffraction pattern of amorphous form of mono-sodium salt is shown in FIG. 4. The error margin in 2θ of the characteristic peaks was ±0.2°
(3) The differential scanning calorimetry thermogram of amorphous form of mono-sodium salt is shown in FIG. 11 which contains the exothermic peak of 214.79° C. The error margin was ±3° C.

Example 5 Crystalline Form A of Mono-Lithium Salt of N-(5-(3-cyanopyrazolo[1,5-α]pyridin-5-yl)-2-methoxypyridin-3-yl)-2,4-difluorobenzenesulfonamide

Preparation of Crystalline Form A of Mono-Lithium Salt

To a mixture of N-(5-(3-cyanopyrazolo[1,5-α]pyridin-5-yl)-2-methoxypyridin-3-yl)-2,4-difluorobenzenesulfonamide (2.00 g, 4.53 mmol) in ethanol (30 mL) was added a solution of lithium hydroxide (141 mg, 5.89 mmol) in ethanol (10 mL) at rt. The mixture was heated to reflux and stirred for 1 h, cooled to room temperature and stirred for 0.5 h, filtered to give the filter cake which was dried at 60° C. for 24 h to obtain a light yellow solid (1.84 g, 90.8%).

Figure 5:
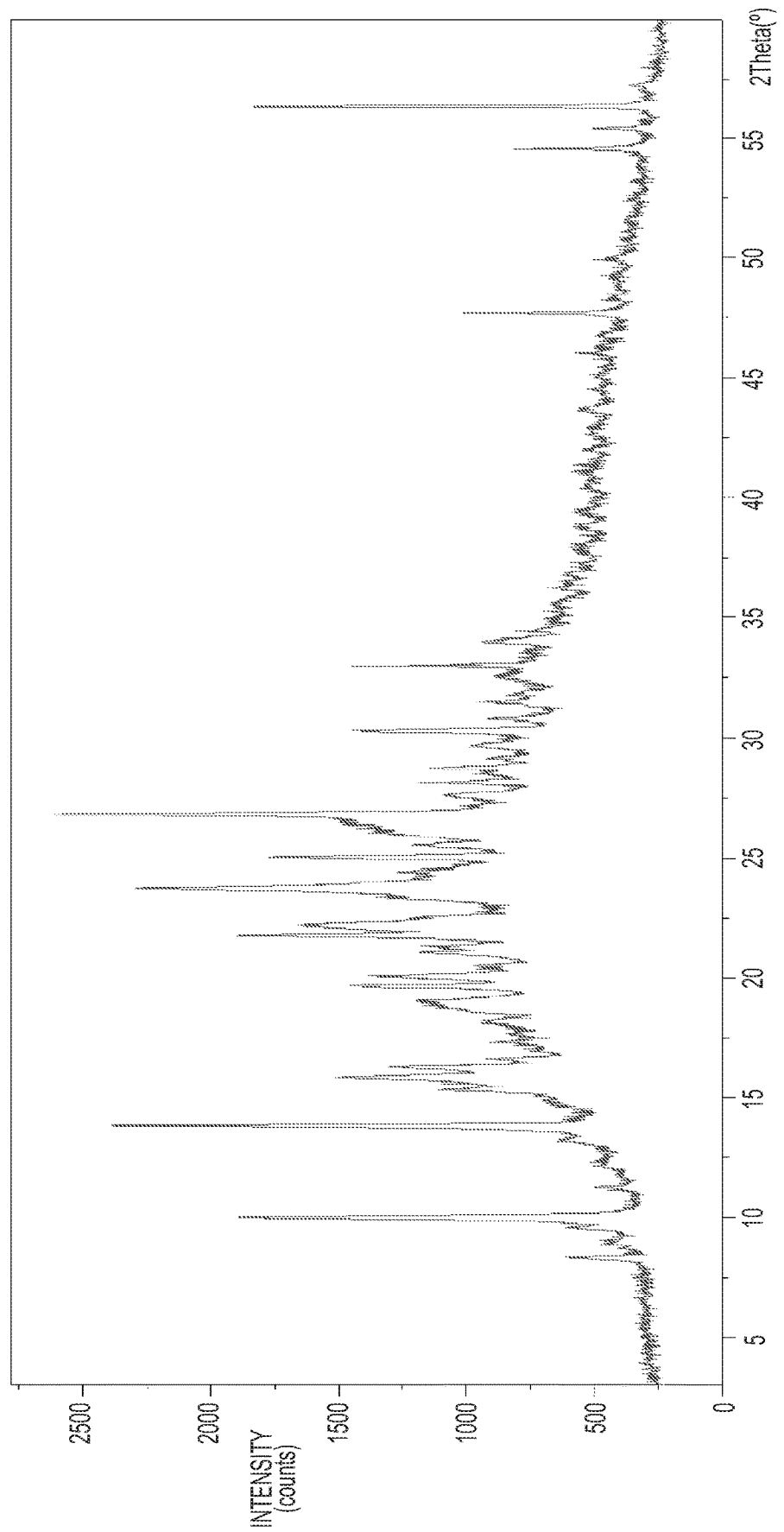
FIG. 5 depicts an X-ray powder diffraction pattern of the crystalline form A of mono-lithium salt of compound of formula (I).
Figure 12:
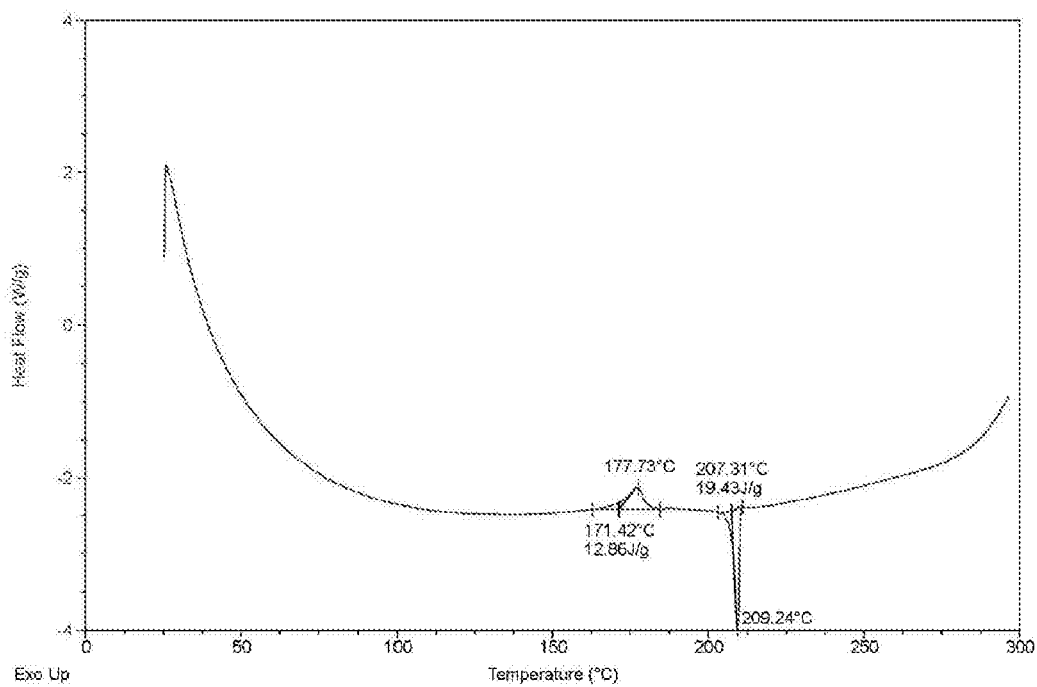
FIG. 12 depicts a differential scanning calorimetry thermogram of the crystalline form A of mono-lithium salt of compound of formula (I).

Identification of Crystalline Form A of Mono-Lithium Salt (1) The salt-forming ratio was 1:1 determined by ICP-MS.
(2) The X-ray powder diffraction pattern of crystalline form A of mono-lithium salt is shown in FIG. 5. The error margin in 2θ of the characteristic peaks was ±0.2°
(3) The differential scanning calorimetry thermogram of crystalline form A of mono-lithium salt is shown in FIG. 12 which contains the endothermic peak of 209.24° C. The error margin was ±3° C.

Example 6 Crystalline Form A of Mono-Potassium Salt of N-(5-(3-cyanopyrazolo[1,5-α]pyridin-5-yl)-2-methoxypyridin-3-yl)-2,4-difluorobenzenesulfonamide

Preparation of Crystalline Form A of Mono-Potassium Salt

To a mixture of N-(5-(3-cyanopyrazolo[1,5-α]pyridin-5-yl)-2-methoxypyridin-3-yl)-2,4-difluorobenzenesulfonamide (2.00 g, 4.53 mmol) in ethanol (30 mL) was added a solution of potassium hydroxide (280 mg, 4.99 mmol) in ethanol (10 mL) at room temperature. The mixture was heated to reflux and stirred for 1 h, then cooled to room temperature and stirred for 0.5 h, filtered to give the filter cake which was dried at 60° C. for 24 h to obtain a light yellow solid (2.11 g, 97.1%).

Figure 6:
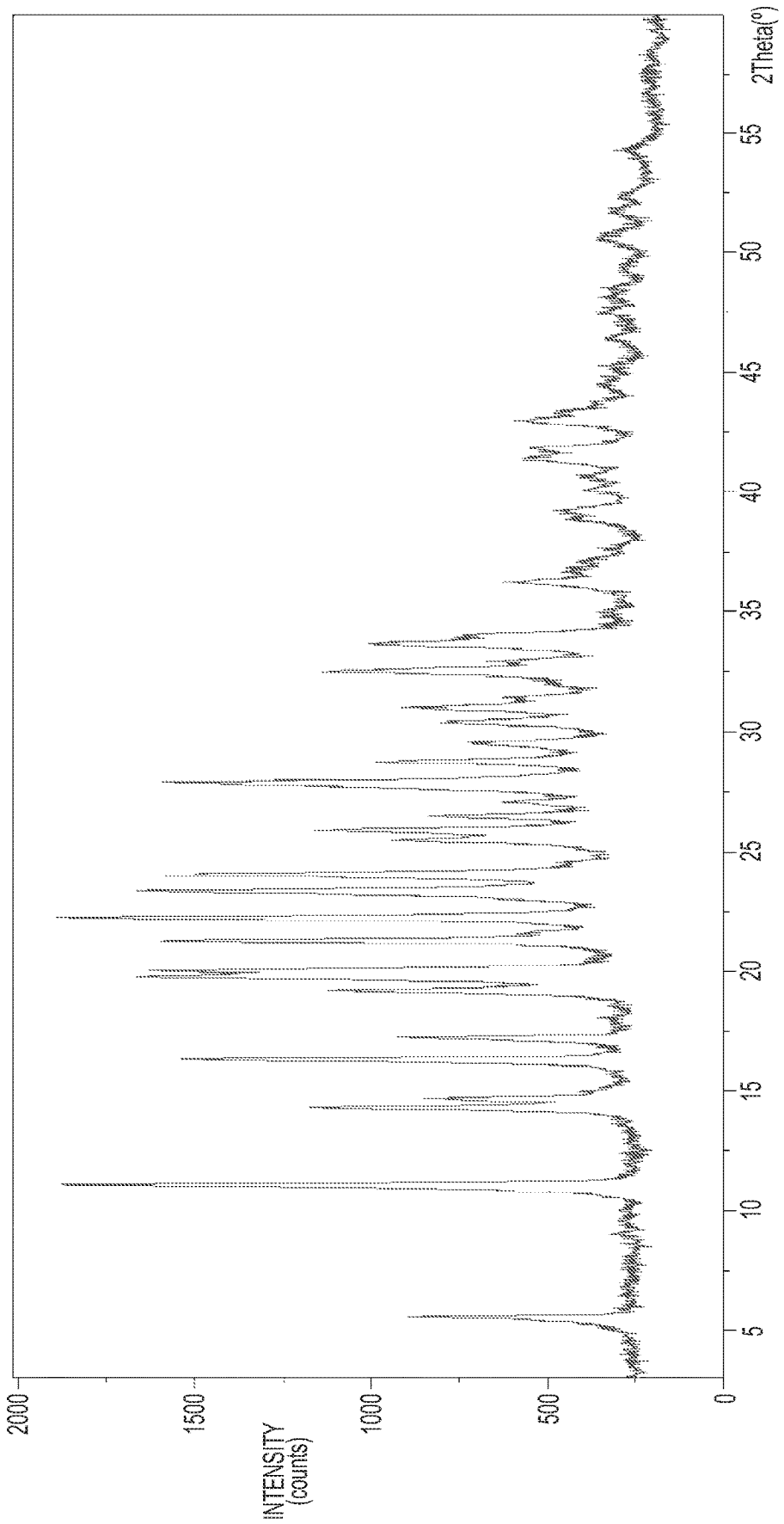
FIG. 6 depicts an X-ray powder diffraction pattern of the crystalline form A of mono-potassium salt of compound of formula (I).
Figure 13:
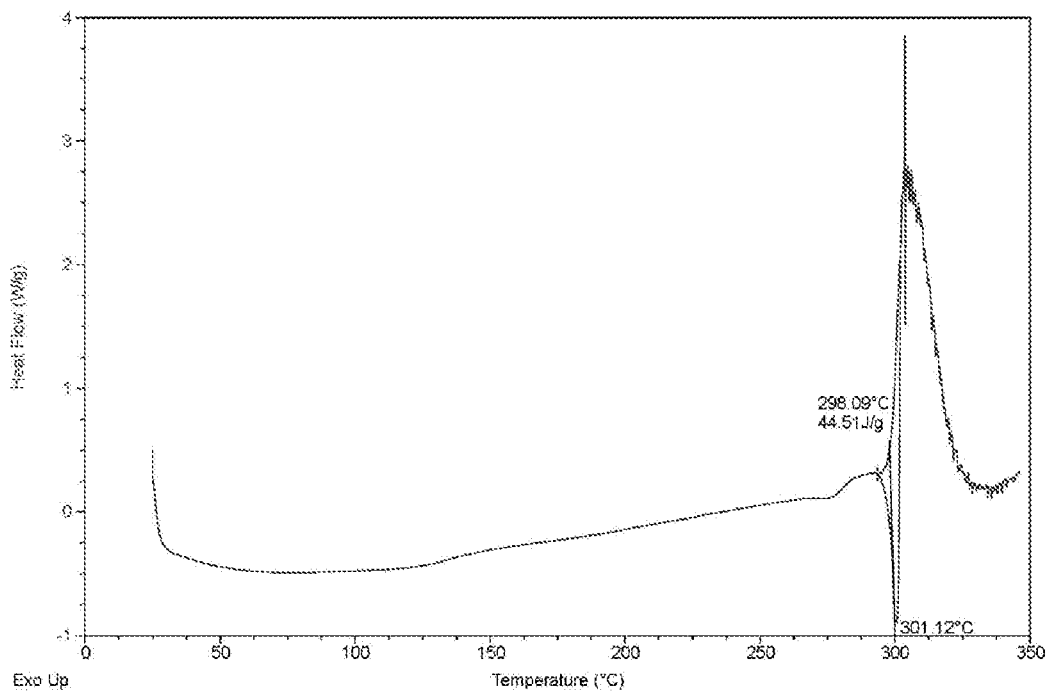
FIG. 13 depicts a differential scanning calorimetry thermogram of the crystalline form A of mono-potassium salt of compound of formula (I).

Identification of Crystalline Form A of Mono-Potassium Salt (1) The salt-forming ratio was 1:1 determined by ICP-MS.
(2) The X-ray powder diffraction pattern of crystalline form A of mono-potassium salt is shown in FIG. 6. The error margin in 2θ of the characteristic peaks was ±0.2°
(3) The differential scanning calorimetry thermogram of crystalline form A of mono-potassium salt is shown in FIG. 13 which contains the endothermic peak of 301.12° C. The error margin was ±3° C.

Example 7 Crystalline Form A of Mono-Choline Salt of N-(5-(3-cyanopyrazolo[1,5-α]pyridin-5-yl)-2-methoxypyridin-3-yl)-2,4-difluorobenzenesulfonamide Preparation of Crystalline Form A of Mono-Choline Salt To a mixture of N-(5-(3-cyanopyrazolo[1,5-α]pyridin-5-yl)-2-methoxypyridin-3-yl)-2,4-difluorobenzenesulfonamide (2.00 g, 4.53 mmol) in ethanol (40 mL) was added a solution of choline in water (1.56 g, 46% w/w, 5.89 mmol) at rt. The mixture was heated to reflux and stirred for 1 h, then cooled to room temperature and stirred for 0.5 h, filtered to give the filter cake which was dried at 60° C. for 24 h to obtain a yellow solid (1.91 g, 77.4%).

Figure 7:
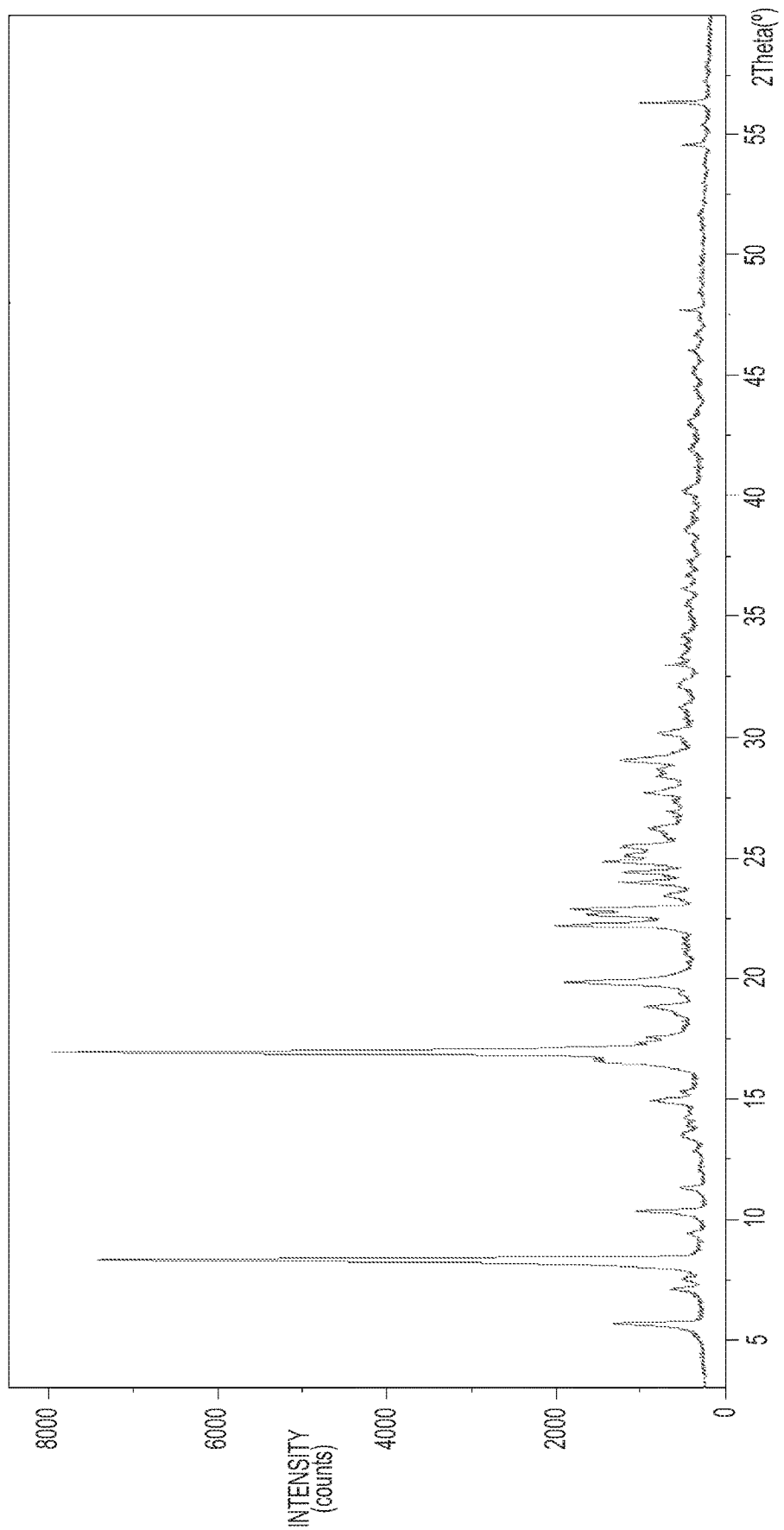
FIG. 7 depicts an X-ray powder diffraction pattern of the crystalline form A of mono-choline salt of compound of formula (I).
Figure 14:
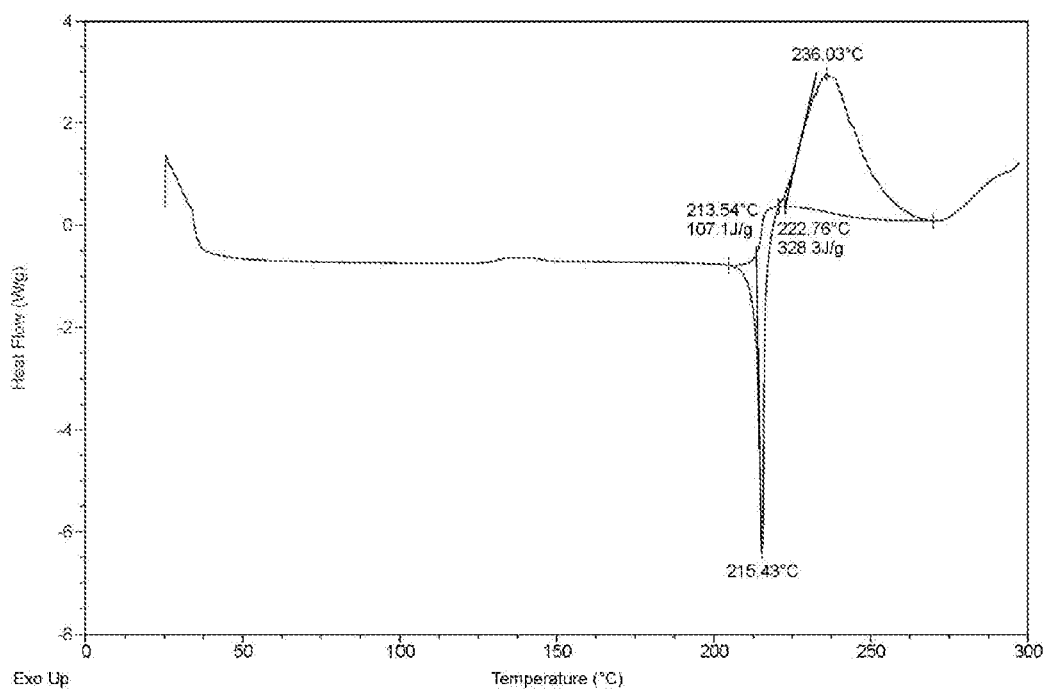
FIG. 14 depicts a differential scanning calorimetry thermogram of the crystalline form A of mono-choline salt of compound of formula (I).

Identification of Crystalline Form A of Mono-Choline Salt (1) The salt-forming ratio was 1:1 determined by $^1$H NMR.
(2) The X-ray powder diffraction pattern of crystalline form A of mono-choline salt is shown in FIG. 7. The error margin in 2θ of the characteristic peaks was ±0.2°.
(3) The differential scanning calorimetry thermogram of crystalline form A of mono-choline salt is shown in FIG. 14 which contains the endothermic peak of 215.43° C. The error margin was ±3° C.

Example 8 Pharmacokinetics Test

The pharmacokinetic properties of amorphous forms or the crystalline forms of base addition salt of Compound (I) disclosed herein were assessed in beagle dogs. The LC/MS/MS system used in the analysis consists of an Agilent 1200 Series vacuum degasser, binary pump, well-plate autosampler, thermostated column compartment, the Agilent G6430 Triple Quadrupole Mass Spectrometer with an electrospray-ionization (ESI) source. Quantitative analysis was carried out using MRM mode. The parameters for MRM transitions are in the Table A.

TABLE A

| MRM | 490.2→383.1 |
|---|---|
| Fragmentor | 230 V |
| CE | 55 V |
| Drying Gas Temp | 350° C. |
| Nebulize | 0.28 MPa |
| Drying Gas Flow | 10 L/min |

An Agilent XDB-C18, 2.1×30 mm, 3.5 μM column was used for the analysis. 5 μL of the samples were injected.

Analysis condition: The mobile phase was 0.1% formic acid in water (A) and 0.1% formic acid in methanol (B). The flow rate was 0.4 mL/min. And the gradient of Mobile phase was in the Table B.

TABLE B

| Time | Gradient of Mobile Phase B |
|---|---|
| 0.5 min | 5% |
| 1.0 min | 95% |
| 2.2 min | 95% |
| 2.3 min | 5% |
| 5.0 min | stop |

Alternatively, an Agilent 6330 series LC/MS/MS spectrometer equipped with G1312A binary pumps, a G1367A autosampler and a G1314C UV detector were used in the analysis. An ESI source was used on the LC/MS/MS spectrometer. The analysis was done in positive ion mode as appropriate and the MRM transition for each analyte was optimized using standard solution. A Capcell MP-C18 100× 4.6 mm I.D., 5 μM column (Phenomenex, Torrance, Calif., USA) was used during the analysis. The mobile phase was 5 mM ammonia acetate, 0.1% MeOH in water (A): 5 mM ammonia acetate, 0.1% MeOH in acetonitrile (B) (70/30, v/v). The flow rate was 0.6 mL/min. Column was maintained at ambient temperature. 20 μL of the samples were injected.

The capsule of amorphous forms or the crystalline forms of base addition salt of Compound (I) mixed with adjuvants respectively was administered by gavage to beagle dogs in a dose of 2.5 mg/kg, 5.0 mg/kg, 7 mg/kg or 10 mg/kg. The blood samples (0.3 mL) were drawn at 0.25, 0.5, 1.0, 2.0, 3.0, 4.0, 6.0, 8.0, 12 and 24 hour time points or 0.083, 0.25, 0.5, 1.0, 2.0, 4.0, 6.0, 8.0 and 24 hour time points and centrifuged at 3,000 or 4000 rpm for 2 to 10 min. The plasma solutions were collected, and analyzed by LC/MS/MS as described above. The pharmacokinetic parameters were calculated according to non-compartment model using WinNonlin procedure. The pharmacokinetic parameters are shown in Table 1.

TABLE 1

Pharmacokinetic profile in beagle dogs

| Example | Dose (mg/kg) | $T_{max}$ (h) | $C_{max}$ (ng/mL) | $AUC_{last}$ (ng · h/mL) |
|---|---|---|---|---|
| crystalline form A of mono-sodium salt | 2.5 | 2.5 | 2820 | 8730 |
| crystalline form B of mono-sodium salt | 2.5 | 0.583 | 4530 | 9370 |
| crystalline form C of mono-sodium salt | 2.5 | 2.33 | 1410 | 5700 |
| amorphous form of mono-sodium salt | 2.5 | 1.33 | 2180 | 7290 |
| crystalline form A of mono-lithium salt | 2.5 | 1.5 | 1640 | 4290 |
| crystalline form A of mono-potassium salt | 2.5 | 0.667 | 3050 | 8420 |
| crystalline form A of mono-choline salt | 2.5 | 1.08 | 3220 | 9130 |
| Compound of formula (I) | 2.5 | 1.67 | 482 | 1550 |

The results listed in Table 1 above show that the values of $C_{max}$ and $AUC_{last}$ of crystalline form A of mono-sodium salt, crystalline form B of mono-sodium salt, crystalline form C of mono-sodium salt, amorphous form of mono-sodium salt, crystalline form A of mono-lithium salt, crystalline form A of mono-potassium salt and crystalline form A of mono-choline salt are much larger than those of compound of formula (I), which indicates that crystalline form A of mono-sodium salt, crystalline form B of mono-sodium salt, crystalline form C of mono-sodium salt, amorphous form of mono-sodium salt, crystalline form A of mono-lithium salt, crystalline form A of mono-potassium salt and crystalline form A of mono-choline salt have good exposure and bioavailability in vivo in beagle dogs.

Example 9 Stability Test

Appropriate amount of sample (100~200 mg) was placed on a watching glass in the form of a thin layer (thickness≤5 mm). The samples were exposed to the following conditions: high temperature (60±2° C.) for 10 days; high humidity (25±2° C., 90%±5% relative humidity) for 10 days; illumination condition (visible light 4500lx±500lx with ultraviolet light not lower than 0.7 W·h/m², 25±2° C., 60%±5% relative humidity) for 10 days; and room temperature (30±2° C., 65%±5% relative humidity) for 10 days, respectively. The impurity contents in the samples were determined at different time points (0, 5 and 10 days) by high performance liquid chromatography (HPLC), and the absorption peaks were normalized relative to the highest peak (corresponds to compound I) which is set to 100%. The instrument and conditions for HPLC are showed in Table 2.

TABLE 2

| Instrument and reagent | Instrument: Agilent 1200 or 1260, One over one hundred thousand of electronic balance, Volumetric flask, 0.45 μm nylon membrane filter; Reagent: Acetonitrile (HPLC), Monopotassium phosphate (AR), Potassium hydroxide (AR), Water (Millipore). |
|---|---|
| Solution Preparation | Blank Solution/Diluent: Mix acetonitrile and water at the ratio of 45/55 (v/v); Sample Solution: Transfer about 33 mg of crystalline form A of compound (I), accurately weighed, to a 100 mL volumetric flask and add diluent to dissolve. Dilute to volume with Diluent and mix well. |
| Chromatographic Conditions | Column: Octadecyl silane bonded silica gel column, 4.6 × 150 mm, 5 μm; Column temperature: 30° C.; Detection wavelength: 235 nm; Flow rate: 1.0 mL/min; Injection volume: 20 μL; Buffer solution: Dissolve 1.361 g of monopotassium phosphate in 1 L of water and mix well. Adjust with potassium hydroxide to a pH of 6.0. Filter the solution and sonicate to obtain buffer Solution; Mobile Phase: Mix Buffer and acetonitrile at the ratio of 55/45 (v/v); Run time: 30 min. |

The results indicated that crystalline forms and amorphous forms of base addition salts of compound of formula (I) had no obvious change in term of appearance and purity under the condition of high temperature (60° C.) and high humidity (25° C., RH 90%±5%). They were steady and suitable for pharmaceutical use.

Example 10 Hygroscopicity Test

A glass weighing bottle equipped with a stopper was tarred and the weight was recorded as $m_1$. Base addition salts of compound (I) in different crystalline forms or amorphous form (about 1.0 g) were placed in the tared weighing bottle and capped with the stopper. The total weight was then recorded as $m_2$. The weighing bottle (without its stopper) was placed in a desiccator containing a saturated solution of ammonium chloride (80%±2% RH (relative humidity)) at 25±1° C. The weighing bottle capped with its stopper was weighed on day 5 and day 10 and the weight was recorded as $m_3$. The hygroscopic capacity was calculate according to the following formula.

$$\text{(Hygroscopic capacity)} = \frac{m_3 - m_2}{m_2 - m_1} \times 100\%$$

The experimental results showed that the base addition salts of compound (I) in different crystalline forms and amorphous form in this invention were not hygroscopic.

Example 11 Solubility Test 0.5 mg of the crystalline forms of base addition salt of Compound (I) was weighed and placed in a 30 mL penicillin bottle, and then 15 mL of purified water was added. The bottle was shook in a 37° C. water bath to observe the dissolution of the sample. If the sample in the bottle was dissolved completely, a little additional sample was added to the solution several times until the solution was saturated and the sample in the bottle was unable to be further dissolved. After the bottle was shook for additional 24 h/48 h, an appropriate amount of 37° C. saturated solution was took from the penicillin bottle and filtered through a membrane filtration (Polyethersulfone, 0.45 m, 13 mm, JINTENG), 2 mL of primary filtrate was discarded, and 600 μL of filtrate and 600 μL of acetonitrile were measured precisely and rapidly, respectively, and then mixed uniformly to obtain the test solution at equilibrium. The solubility of the sample was detected by external standard method.

The chromatographic column used in the analysis was Agilent ZORBAX SB-C18, 4.6×50 mm, 5 μM (or other suitable chromatographic column), the detector was UV detector with detection wavelength of 264 nm, the flow rate was 1.0 mL/min, the column temperature was 35° C., the injection volume was 10 μL, the mobile phases were 10 mM sodium dihydrogen phosphate buffer (pH 3.0) and acetonitrile (V:V=50:50), the running time was 7 min.

Conclusion: The experimental results showed that all the crystalline forms of base addition salt of Compound (I) have good solubility.

The foregoing disclosure has been described in some detail by way of illustration and example, for purposes of clarity and understanding. The invention has been described with reference to various specific and preferred embodiments and techniques. However, it should be understood that many variations and modifications can be made while remaining within the spirit and scope of the invention. It will be obvious to one of skill in the art that changes and modifications can be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

What is claimed is:

1. A pharmaceutically acceptable base addition salt of a compound of Formula (I):

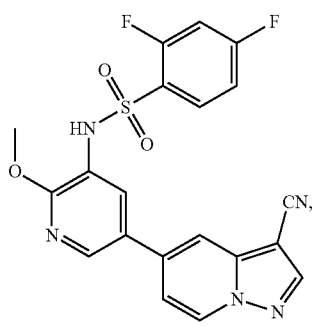

(I)

wherein,
the base addition salt is crystalline form A of mono-sodium salt of compound of formula (I) having an X-ray powder diffraction pattern comprising 2θ values at 14.73°±0.2°, 14.93°±0.2°, 21.77°±0.2°, 22.59°±0.2°, 23.29°±0.2° and 24.87°±0.2°; or
the base addition salt is crystalline form B of mono-sodium salt of compound of formula (I) having an X-ray powder diffraction pattern comprising 2θ values at 8.75°±0.2°, 12.27°±0.2°, 14.42°±0.2°, 20.46°±0.2°, 23.64°±0.2°, 25.14°±0.2° and 25.89°±0.2°; or
the base addition salt is crystalline form C of mono-sodium salt of compound of formula (I) having an X-ray powder diffraction pattern comprising 2θ values at 10.52°±0.2°, 13.64°±0.2°, 14.40°±0.2°, 15.86°±0.2°, 18.72°±0.2°, 19.14°±0.2° and 24.68°±0.2°; or
the base addition salt is an amorphous form of mono-sodium salt of compound of formula (I) having an X-ray powder diffraction (XRPD) pattern substantially in accordance with the pattern shown in FIG. 4; or
the base addition salt is crystalline form A of mono-lithium salt of compound of formula (I) having an X-ray powder diffraction pattern comprising 2θ values at 9.98°±0.2°, 13.82°±0.2°, 21.74°±0.2°, 23.70°±0.2°, 25.03°±0.2°, 26.82°±0.2° and 32.96°±0.2°; or
the base addition salt is crystalline form A of mono-potassium salt of compound of formula (I) having an X-ray powder diffraction pattern comprising 2θ values at 11.04°±0.2°, 16.29°±0.2°, 19.75°±0.2°, 21.26°±0.2°, 22.22°±0.2° and 23.33°±0.2°; or
the base addition salt is crystalline form A of mono-choline salt of compound of formula (I) having an X-ray powder diffraction pattern comprising 2θ values at 8.31°±0.2°, 16.94°±0.2°, 19.82°±0.2°, 22.20°±0.2°, 22.63°±0.2° and 22.85°±0.2°.

2. The base addition salt according to claim 1, wherein the mono-sodium salt is crystalline form A of mono-sodium salt of compound of formula (I) having an X-ray powder diffraction pattern comprising 2θ values at 10.71°±0.2°, 14.73°±0.2°, 14.93°±0.2°, 19.01°±0.2°, 19.41°±0.2°, 21.57°±0.2°, 21.77°±0.2°, 22.59°±0.2°, 23.29°±0.2°, 24.87°±0.2°, 28.36°±0.2° and 30.18°±0.2°; or
the mono-sodium salt is crystalline form B of mono-sodium salt of compound of formula (I) having an X-ray powder diffraction pattern comprising 2θ values at 8.75°±0.2°, 12.27°±0.2°, 14.42°±0.2°, 15.62°±0.2°, 20.46°±0.2°, 23.32°±0.2°, 23.64°±0.2°, 25.14°±0.2°, 25.89°±0.2°, 26.87°±0.2°, 27.43°±0.2°, 28.09°±0.2°, 32.95°±0.2° and 36.47°±0.2°; or
the mono-sodium salt is crystalline form C of mono-sodium salt of compound of formula (I) having an X-ray powder diffraction pattern comprising 2θ values at 10.52°±0.2°, 13.64°±0.2°, 14.40°±0.2°, 15.86°±0.2°, 18.72°±0.2°, 19.14°±0.2°, 19.47°±0.2°, 20.31°±0.2°, 21.16°±0.2°, 23.94°±0.2°, 24.68°±0.2°, 26.21°±0.2° and 29.03°±0.2°; or
the lithium salt is crystalline form A of mono-lithium salt of compound of formula (I) having an X-ray powder diffraction pattern comprising 2θ values at 9.98°±0.2°, 13.82°±0.2°, 15.83°±0.2°, 16.25°±0.2°, 19.64°±0.2°, 20.02°±0.2°, 21.74°±0.2°, 22.16°±0.2°, 23.70°±0.2°, 25.03°±0.2°, 26.38°±0.2°, 26.82°±0.2°, 30.27°±0.2° and 32.96°±0.2°; or
the potassium salt is crystalline form A of mono-potassium salt of compound of formula (I) having an X-ray powder diffraction pattern comprising 2θ values at 11.04°±0.2°, 14.28°±0.2°, 16.29°±0.2°, 19.75°±0.2°, 20.01°±0.2°, 21.26°±0.2°, 22.22°±0.2°, 23.33°±0.2°, 24.02°±0.2°, 25.87°±0.2°, 27.83°±0.2° and 32.47°±0.2°; or
the choline salt is crystalline form A of mono-choline salt of compound of formula (I) having an X-ray powder diffraction pattern comprising 2θ values at 5.65°±0.2°, 8.31°±0.2°, 10.31°±0.2°, 16.53°±0.2°, 16.94°±0.2°, 17.27°±0.2°, 19.82°±0.2°, 22.20°±0.2°, 22.63°±0.2°, 22.85°±0.2°, 23.97°±0.2°, 24.81°±0.2° and 29.07°±0.2°.

3. The base addition salt according to claim 2, wherein the mono-sodium salt is crystalline form A of mono-sodium salt of compound of formula (I) having an X-ray powder diffraction pattern comprising 2θ values at 5.59°±0.2°, 9.33°±0.2°, 10.71°±0.2°, 11.21°±0.2°, 14.73°±0.2°, 14.93°±0.2°, 15.39°±0.2°, 16.55°±0.2°, 17.36°±0.2°, 17.64°±0.2°, 18.42°±0.2°, 19.01°±0.2°, 19.41°±0.2°, 19.66°±0.2°, 19.84°±0.2°, 20.26°±0.2°, 21.57°±0.2°, 21.77°±0.2°, 22.34°±0.2°, 22.59°±0.2°, 23.29°±0.2°, 24.15°±0.2°, 24.87°±0.2°, 25.59°±0.2°, 26.26°±0.2°, 26.75°±0.2°, 27.32°±0.2°, 27.87°±0.2°, 28.36°±0.2°, 28.71°±0.2°, 29.08°±0.2°, 29.59°±0.2°, 30.18°±0.2°, 30.56°±0.2°, 31.01°±0.2°, 31.61°±0.2°, 31.81°±0.2°, 32.14°±0.2°, 32.72°±0.2°, 33.26°±0.2°, 34.14°±0.2°, 35.97°±0.2°, 36.46°±0.2°, 38.40°±0.2°, 38.83°±0.2°, 39.49°±0.2°, 40.04°±0.2°, 41.32°±0.2°, 42.80°±0.2°, 43.89°±0.2° and 45.77°±0.2°; or
the mono-sodium salt is crystalline form B of mono-sodium salt of compound of formula (I) having an X-ray powder diffraction pattern comprising 2θ values at 7.23°±0.2°, 8.75°±0.2°, 12.27°±0.2°, 12.88°±0.2°, 13.94°±0.2°, 14.42°±0.2°, 14.87°±0.2°, 15.62°±0.2°, 17.85°±0.2°, 18.51°±0.2°, 18.94°±0.2°, 19.33°±0.2°, 19.79°±0.2°, 20.46°±0.2°, 21.50°±0.2°, 22.23°±0.2°, 22.79°±0.2°, 23.32°±0.2°, 23.64°±0.2°, 24.67°±0.2°, 25.14°±0.2°, 25.89°±0.2°, 26.87°±0.2°, 27.43°±0.2°, 28.09°±0.2°, 28.54°±0.2°, 29.02°±0.2°, 29.48°±0.2°, 29.96°±0.2°, 30.74°±0.2°, 31.56°±0.2°, 32.95°±0.2°, 33.50°±0.2°, 35.86°±0.2°, 36.47°±0.2°, 37.32°±0.2°, 39.11°±0.2°, 39.84°±0.2°, 42.23°±0.2°, 42.93°±0.2° and 44.44°±0.2°; or
the mono-sodium salt is crystalline form C of mono-sodium salt of compound of formula (I) having an X-ray powder diffraction pattern comprising 2θ values at 5.24°±0.2°, 5.61°±0.2°, 8.88°±0.2°, 9.54°±0.2°, 10.52°±0.2°, 13.64°±0.2°, 14.40°±0.2°, 14.78°±0.2°, 15.86°±0.2°, 16.46°±0.2°, 16.95°±0.2°, 17.86°±0.2°, 18.72°±0.2°, 19.14°±0.2°, 19.47°±0.2°, 20.31°±0.2°, 20.74°±0.2°, 21.16°±0.2°, 22.09°±0.2°, 22.61°±0.2°, 23.94°±0.2°, 24.29°±0.2°, 24.68°±0.2°, 26.21°±0.2°, 27.03°±0.2°, 27.60°±0.2°, 28.32°±0.2°, 29.03°±0.2°, 30.10°±0.2°, 31.73°±0.2°, 31.94°±0.2°, 33.86°±0.2°, 34.33°±0.2°, 35.60°±0.2°, 36.01°±0.2°, 36.95°±0.2°, 38.02°±0.2°, 38.86°±0.2°, 40.32°±0.2°, 41.00°±0.2°, 42.08°±0.2° and 44.21°±0.2°; or the lithium salt is crystalline form A of mono-lithium salt of compound of formula (I) having an X-ray powder diffraction pattern comprising 2θ values at 3.60°±0.2°, 8.33°±0.2°, 8.97°±0.2°, 9.58°±0.2°, 9.98°±0.2°, 11.25°±0.2°, 12.24°±0.2°, 13.26°±0.2°, 13.82°±0.2°, 15.34°±0.2°, 15.83°±0.2°, 16.25°±0.2°, 16.61°±0.2°, 17.31°±0.2°, 18.06°±0.2°, 18.90°±0.2°, 19.64°±0.2°, 20.02°±0.2°, 21.02°±0.2°, 21.28°±0.2°, 21.74°±0.2°, 22.16°±0.2°, 23.70°±0.2°, 24.37°±0.2°, 25.03°±0.2°, 25.52°±0.2°, 26.38°±0.2°, 26.82°±0.2°, 27.59°±0.2°, 28.15°±0.2°, 28.74°±0.2°, 29.30°±0.2°, 29.69°±0.2°, 30.27°±0.2°, 30.82°±0.2°, 31.45°±0.2°, 32.60°±0.2°, 32.96°±0.2°, 33.96°±0.2°, 36.26°±0.2°, 37.86°±0.2°, 38.76°±0.2°, 39.40°±0.2°, 41.02°±0.2°, 41.98°±0.2°, 42.73°±0.2° and 43.64°±0.2°; or the potassium salt is crystalline form A of mono-potassium salt of compound of formula (I) having an X-ray powder diffraction pattern comprising 2θ values at 5.53°±0.2°, 11.04°±0.2°, 14.28°±0.2°, 14.67°±0.2°, 16.29°±0.2°, 17.19°±0.2°, 19.18°±0.2°, 19.75°±0.2°, 20.01°±0.2°, 21.26°±0.2°, 21.61°±0.2°, 22.22°±0.2°, 23.33°±0.2°, 24.02°±0.2°, 25.47°±0.2°, 25.87°±0.2°, 26.46°±0.2°, 27.07°±0.2°, 27.83°±0.2°, 28.76°±0.2°, 29.49°±0.2°, 30.37°±0.2°, 31.01°±0.2°, 32.47°±0.2°, 32.96°±0.2°, 33.64°±0.2°, 33.98°±0.2°, 36.27°±0.2°, 38.87°±0.2°, 39.22°±0.2°, 40.59°±0.2°, 41.36°±0.2°, 41.77°±0.2°, 43.03°±0.2°, 44.51°±0.2°, 46.39°±0.2°, 47.48°±0.2°, 48.26°±0.2°, 50.58°±0.2°, 51.71°±0.2° and 54.23°±0.2°; or the choline salt is crystalline form A of mono-choline salt of compound of formula (I) having an X-ray powder diffraction pattern comprising 2θ values at 5.65°±0.2°, 7.12°±0.2°, 7.52°±0.2°, 8.31°±0.2°, 9.40°±0.2°, 10.31°±0.2°, 11.29°±0.2°, 13.51°±0.2°, 14.92°±0.2°, 15.29°±0.2°, 16.53°±0.2°, 16.94°±0.2°, 17.27°±0.2°, 17.50°±0.2°, 18.80°±0.2°, 19.82°±0.2°, 22.20°±0.2°, 22.63°±0.2°, 22.85°±0.2°, 23.42°±0.2°, 23.97°±0.2°, 24.39°±0.2°, 24.81°±0.2°, 25.11°±0.2°, 25.45°±0.2°, 26.19°±0.2°, 26.95°±0.2°, 27.70°±0.2°, 28.52°±0.2°, 29.07°±0.2°, 30.15°±0.2°, 31.21°±0.2°, 32.12°±0.2°, 32.95°±0.2°, 33.33°±0.2°, 34.15°±0.2°, 35.49°±0.2°, 36.11°±0.2°, 38.57°±0.2°, 40.18°±0.2°, 41.92°±0.2° and 42.99°±0.2°.

4. The base addition salt according to claim 2, wherein the mono-sodium salt is crystalline form A of mono-sodium salt of compound of formula (I) having an X-ray powder diffraction (XRPD) pattern substantially in accordance with the pattern shown in FIG. 1; or
the mono-sodium salt is crystalline form B of mono-sodium salt of compound of formula (I) having an X-ray powder diffraction (XRPD) pattern substantially in accordance with the pattern shown in FIG. 2; or
the mono-sodium salt is crystalline form C of mono-sodium salt of compound of formula (I) having an X-ray powder diffraction (XRPD) pattern substantially in accordance with the pattern shown in FIG. 3; or
the lithium salt is crystalline form A of mono-lithium salt of compound of formula (I) having an X-ray powder diffraction (XRPD) pattern substantially in accordance with the pattern shown in FIG. 5; or
the potassium salt is crystalline form A of mono-potassium salt of compound of formula (I) having an X-ray powder diffraction (XRPD) pattern substantially in accordance with the pattern shown in FIG. 6; or
the choline salt is crystalline form A of mono-choline salt of compound of formula (I) having an X-ray powder diffraction (XRPD) pattern substantially in accordance with the pattern shown in FIG. 7.

5. A pharmaceutical composition comprising the base addition salt of claim 1 and a pharmaceutically acceptable carrier, excipient, diluents, adjuvant, or a combination thereof.

6. The pharmaceutical composition according to claim 5 further comprising an additional therapeutic agent selected from a chemotherapeutic agent, an anti-proliferative agent, an agent for treating atherosclerosis, an agent for treating lung fibrosis or a combination thereof.

7. The pharmaceutical composition according to claim 6, wherein the additional therapeutic agent is chlorambucil, melphalan, cyclophosphamide, ifosfamide, busulfan, carmustine, lomustine, streptozocin, cisplatin, carboplatin, oxaliplatin, dacarbazine, temozolomide, procarbazine, methotrexate, fluorouracil, cytarabine, gemcitabine, mercaptopurine, fludarabine, vinblastine, vincristine, vinorelbine, paclitaxel, docetaxel, topotecan, irinotecan, etoposide, trabectedin, dactinomycin, doxorubicin, epirubicin, daunorubicin, mitoxantrone, bleomycin, mitomycin, ixabepilone, tamoxifen, flutamide, gonadorelin analogues, megestrol, prednidone, dexamethasone, methylprednisolone, thalidomide, interferon alfa, leucovorin, sirolimus, temsirolimus, everolimus, afatinib, alisertib, amuvatinib, apatinib, axitinib, bortezomib, bosutinib, brivanib, cabozantinib, cediranib, crenolanib, crizotinib, dabrafenib, dacomitinib, danusertib, dasatinib, erlotinib, ganetespib, gefitinib, ibrutinib, icotinib, imatinib, iniparib, lapatinib, lenvatinib, lmasitinib, neratinib, nilotinib, niraparib, oprozomib, olaparib, pazopanib, ponatinib, quizartinib, regorafenib, rigosertib, rucaparib, ruxolitinib, saracatinib, saridegib, sorafenib, sunitinib, tasocitinib, telatinib, tivozanib, tofacitinib, trametinib, vandetanib, veliparib, vemurafenib, vismodegib, alemtuzumab, bevacizumab, brentuximab vedotin, catumaxomab, cetuximab, denosumab, gemtuzumab, ipilimumab, nimotuzumab, ofatumumab, panitumumab, ramucirumab, rituximab, trastuzumab, or a combination thereof.

8. The base addition salt according to claim 1, wherein the base addition salt is not hygroscopic.

* * * * *